United States Patent
Yagyu et al.

(10) Patent No.: US 11,661,408 B2
(45) Date of Patent: *May 30, 2023

(54) FLUORINE-CONTAINING ETHER COMPOUND, LUBRICANT FOR MAGNETIC RECORDING MEDIUM, AND MAGNETIC RECORDING MEDIUM

(71) Applicant: SHOWA DENKO K.K., Tokyo (JP)

(72) Inventors: Daisuke Yagyu, Ichihara (JP); Naoya Fukumoto, Ichihara (JP); Tsuyoshi Kato, Ichihara (JP); Katsumi Murofushi, Ichihara (JP)

(73) Assignee: SHOWA DENKO K.K., Tokyo (JP)

( * ) Notice: Subject to any disclaimer, the term of this patent is extended or adjusted under 35 U.S.C. 154(b) by 169 days.

This patent is subject to a terminal disclaimer.

(21) Appl. No.: 17/274,702

(22) PCT Filed: Aug. 28, 2019

(86) PCT No.: PCT/JP2019/033700
§ 371 (c)(1),
(2) Date: Mar. 9, 2021

(87) PCT Pub. No.: WO2020/054420
PCT Pub. Date: Mar. 19, 2020

(65) Prior Publication Data
US 2022/0048882 A1 Feb. 17, 2022

(30) Foreign Application Priority Data
Sep. 12, 2018 (JP) ............... JP2018-170365

(51) Int. Cl.
*C07D 333/16* (2006.01)
*G11B 5/725* (2006.01)
(Continued)

(52) U.S. Cl.
CPC ......... *C07D 333/16* (2013.01); *C10M 107/38* (2013.01); *G11B 5/7257* (2020.08); *G11B 5/7266* (2020.08); *C10N 2040/18* (2013.01)

(58) Field of Classification Search
CPC ..... G11B 5/725; G11B 5/7257; G11B 5/7266; C10M 107/38; C10M 107/46;
(Continued)

(56) References Cited

U.S. PATENT DOCUMENTS

| 6,323,163 B1 | 11/2001 | Sasaki et al. |
| 11,011,200 B2 | 5/2021 | Uetake et al. |

(Continued)

FOREIGN PATENT DOCUMENTS

| JP | 11-60720 A | 3/1999 |
| JP | 5465454 B2 | 11/2009 |

(Continued)

OTHER PUBLICATIONS

International Search Report for PCT/JP2019/033700 dated Nov. 12, 2019 [PCT/ISA/210].

(Continued)

*Primary Examiner* — Holly Rickman
(74) *Attorney, Agent, or Firm* — Sughrue Mion, PLLC

(57) ABSTRACT

The fluorine-containing ether compound is represented by the following formula (1): $R^1$—$R^2$—$CH_2$—$R^3$—$CH_2$—$R^4$. In the formula (1), $R^1$ is represented by the following formula (2), $R^2$ is represented by the following formula (3), $R^3$ is a perfluoropolyether chain, and $R^4$ is an organic end group different from $R^1$—$R^2$— and contains two or three polar groups, wherein each polar group is bonded to a different carbon atom, and the carbon atoms to which the polar groups are bonded are bonded to one another via a linking group containing a carbon atom to which the polar (Continued)

group is not bonded. In the formula (2), r is 1 to 3. In the formula (3), w is 2 or 3.

[Chemical Formula 1]

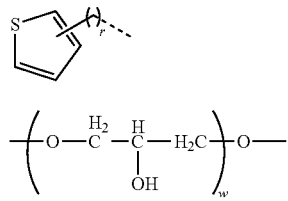

(2)

(3)

11 Claims, 1 Drawing Sheet

(51) Int. Cl.
*C10M 107/38* (2006.01)
*G11B 5/72* (2006.01)
*C10N 40/18* (2006.01)

(58) Field of Classification Search
CPC ...... C10M 2221/0405; C10M 2213/00; C10N 2040/18; C10N 2020/04; C07D 333/10; C07D 333/12; C07D 333/16; C07D 333/18; C08G 65/334
See application file for complete search history.

(56) References Cited

U.S. PATENT DOCUMENTS

| | | | | |
|---|---|---|---|---|
| 11,427,779 | B2* | 8/2022 | Yamaguchi | C07D 333/16 |
| 2006/0111251 | A1 | 5/2006 | Tonelli et al. | |
| 2010/0261039 | A1 | 10/2010 | Itoh et al. | |
| 2012/0008228 | A1 | 1/2012 | Mabuchi et al. | |
| 2013/0209837 | A1 | 8/2013 | Sagata et al. | |
| 2015/0371672 | A1 | 12/2015 | Sagata | |

| | | | |
|---|---|---|---|
| 2019/0084911 | A1 | 3/2019 | Yagyu et al. |
| 2019/0185621 | A1 | 6/2019 | Naitou et al. |
| 2019/0382676 | A1 | 12/2019 | Yamaguchi et al. |

FOREIGN PATENT DOCUMENTS

| | | | |
|---|---|---|---|
| JP | 2010-143855 | A | 7/2010 |
| JP | 4632144 | B2 | 2/2011 |
| JP | 2012-009090 | A | 1/2012 |
| JP | 2012-33253 | A | 2/2012 |
| JP | 2013-163667 | A | 8/2013 |
| JP | 2013-181014 | A | 9/2013 |
| JP | 2013-181140 | A | 9/2013 |
| JP | 5613916 | B2 | 10/2014 |
| JP | 5909837 | B2 | 4/2016 |
| JP | 2018-035348 | A | 3/2018 |
| WO | 98/17617 | A1 | 4/1998 |
| WO | 2009/123043 | A1 | 10/2009 |
| WO | 2011/099131 | A1 | 8/2011 |
| WO | 2015/087615 | A1 | 6/2015 |
| WO | 2017/154403 | A1 | 9/2017 |
| WO | 2018/139174 | A1 | 8/2018 |
| WO | 2019/039200 | A1 | 2/2019 |
| WO | 2019/087548 | A1 | 5/2019 |

OTHER PUBLICATIONS

Notice of Reasons for Rejection dated Dec. 24, 2019, from the Japanese Patent Office in Application No. 2016-133653.
Final Office Action dated Nov. 12, 2020 issued in U.S. Appl. No. 15/640,729.
International Search Report for PCT/JP2018/000071 dated Mar. 6, 2018 [PCT/ISA/210].
Non-Final Office Action dated May 13, 2020 issued in U.S. Appl. No. 15/640,729.
Non-Final Office Action dated Oct. 29, 2019 issued in U.S. Appl. No. 15/640,729.
Notice of Allowance dated Feb. 8, 2021 issued in U.S. Appl. No. 15/640,729.
Requirement for Election/Restriction dated Jun. 10, 2019 issued in U.S. Appl. No. 15/640,729.
Supplemental Notice of Allowability dated Mar. 4, 2021 issued in U.S. Appl. No. 15/640,729.
Office Action dated Jun. 21, 2021 in U.S. Appl. No. 16/480,483.
Office Action dated Jan. 19, 2022 in U.S. Appl. No. 16/480,483.
Notice of Allowance dated May 5, 2022 in U.S. Appl. No. 16/480,483.

* cited by examiner

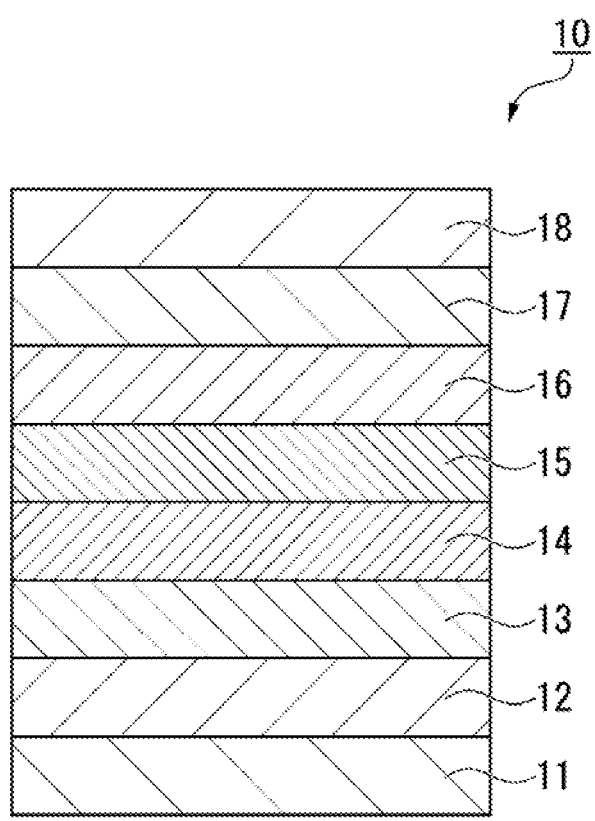

FLUORINE-CONTAINING ETHER COMPOUND, LUBRICANT FOR MAGNETIC RECORDING MEDIUM, AND MAGNETIC RECORDING MEDIUM

CROSS REFERENCE TO RELATED APPLICATIONS

This application is a National Stage of International Application No. PCT/JP2019/033700 filed Aug. 28, 2019, claiming priority based on Japanese Patent Application No. 2018-170365 filed Sep. 12, 2018, the contents of which are incorporated herein by reference.

BACKGROUND OF THE INVENTION

Field of the Invention

The present invention relates to a fluorine-containing ether compound suitable for use as a lubricant for magnetic recording media, a lubricant for magnetic recording media containing the same, and a magnetic recording medium.

Description of Related Art

In recent years, as information processing capacity increases, various information recording technologies have been developed. In particular, a magnetic recording medium suitable for high recording density has been developed.

Conventionally, in a magnetic recording medium, a protective layer and a lubricant layer are provided on the magnetic recording layer formed on the substrate in order to ensure the durability and reliability of the magnetic recording medium. In particular, various characteristics such as long-term stability, chemical substance resistance (preventing contamination such as siloxane) and wear resistance are required for the lubricant layer provided for the outermost surface.

Conventionally, as a lubricant for magnetic recording media, a lubricant containing a compound having a polar group such as a hydroxy group at the end of a fluorine polymer having a repeating structure containing $CF_2$ has been proposed. (For example, see Patent Documents 1 to 3)

For example, Patent Document 1 discloses a compound in which a substituent, having a plurality of hydroxy groups and having a shortest distance of 3 atoms or more between the hydroxy groups, is provided at both end portions.

Patent Document 2 discloses a fluoropolyether compound having an aromatic group at one end and a hydroxy group at the other end.

Patent Document 3 discloses a compound having a perfluoropolyether main chain, having an aromatic group and a hydroxy group at the ends of the molecule, wherein the aromatic group and the hydroxy group are bonded to different carbon atoms.

Further, Patent Document 4 discloses a fluorine-containing ether compound in which an end group containing an organic group having at least one double bond or triple bond is arranged on one end of a perfluoropolyether chain through a divalent linking group bonded by an ethereal oxygen; and another end group which contains two or three polar groups is arranged on the other end of the perfluoropolyether chain, wherein each polar group is bonded to a different carbon atom, and carbon atoms bonded to the polar group are bonded to one another through a linking group containing a carbon atom not bonded to the polar group.

In recent years, a magnetic head having a heater made of a thin film resistor inside a write element (DFH element) is generally used. In such a magnetic head, a tip of the write element projects by thermal expansion due to heating by the heater, thereby making the write element closer to the surface of the disk (magnetic recording medium).

In this technique, the heater power (mW in units) required for the tip of the write element to thermally expand and contact (touchdown) the disk surface is called a touchdown power (TDp). The larger the TDp, in other words, the larger the protrusion amount of the tip of the write element due to thermal expansion, the closer the magnetic head can be to the disk surface. As a result, the magnetic spacing between the magnetic head and the magnetic layer of the magnetic recording medium can be reduced, and the recording capacity of the magnetic recording medium can be improved.

PATENT DOCUMENT

[Patent Document 1] Japanese Patent No. 4632144
[Patent Document 2] Japanese Patent No. 5909837
[Patent Document 3] Japanese Patent No. 5465454
[Patent Document 4] International Publication WO 2017/154403

SUMMARY OF THE INVENTION

In recent years, with the rapid improvement of information recording density of a magnetic recording medium, a reduction of magnetic spacing between a magnetic head and a magnetic layer of the magnetic recording medium has been demanded. Therefore, a further reduction in thickness is required for a lubricant layer existing between the magnetic head and the magnetic layer of the magnetic recording medium.

In addition, due to diversification of applications of magnetic recording media, environmental resistance required for magnetic recording media has become extremely severe. Therefore, it is required that wear resistance and chemical substance resistance of the lubricant layer, which greatly affects the reliability of the magnetic recording medium, are further improved.

However, in general, when the thickness of the lubricant layer is reduced, the coating property of the lubricant layer is reduced, and the chemical substance resistance and wear resistance of the lubricant layer are deteriorated. Therefore, it has been difficult not only to ensure chemical substance resistance and wear resistance but also to reduce the thickness (reduction of magnetic spacing) of the lubricant layer.

Further, in order to reduce the magnetic spacing, it is required to increase the touchdown power (TDp). In order to increase TDp, it is important to make the surface of the magnetic recording medium smooth. Therefore, it is required to suppress surface unevenness in the lubricant layer disposed on the outermost surface of the magnetic recording medium.

The present invention has been made in view of the above circumstances, and an object of the present invention is to provide a fluorine-containing ether compound capable of forming a lubricant layer having excellent chemical substance resistance and wear resistance and having suppressed surface unevenness even when the thickness is small, which can be suitably used as a material for a lubricant for magnetic recording media.

Another object of the present invention is to provide a lubricant for magnetic recording medium containing the fluorine-containing ether compound of the present invention.

Another object of the present invention is to provide a magnetic recording medium having excellent reliability and durability and having a lubricant layer containing the fluorine-containing ether compound of the present invention.

Means for Solving the Problems

The present inventors have conducted extensive research to solve the above problems.

As a result, it has been found that a lubricant layer having excellent chemical substance resistance and wear resistance and suppressed surface unevenness can be formed even when the thickness is thin by using a lubricant for magnetic recording media, which contains a fluorine-containing ether compound having a specific molecular structure.

That is, the present invention relates to the following matters.

[1] A fluorine-containing ether compound represented by the following formula (1),

 (1)

wherein in the formula (1), $R^1$ is represented by the following formula (2);
$R^2$ is represented by the following formula (3);
$R^3$ is a perfluoropolyether chain; and
$R^4$ is an organic end group different from $R^1$—$R^2$— and comprises two or three polar groups, wherein each polar group is bonded to a different carbon atom, and the carbon atoms to which the polar groups are bonded are bonded to one another via a linking group containing a carbon atom to which the polar group is not bonded,

[Chemical Formula 1]

 (2)

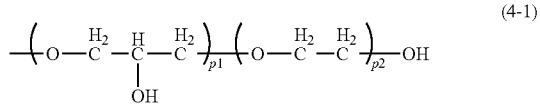 (3)

wherein in the formula (2), r represents an integer of 1 to 3; and
in the formula (3), w represents 2 or 3.

[2] The fluorine-containing ether compound according to [1], wherein all the polar groups of $R^4$ in the formula (1) are hydroxyl groups.

[3] The fluorine-containing ether compound according to [1] or [2], wherein $R^4$ in the formula (1) is an end group represented by any one of the following formulae (4-1) to (4-4),

[Chemical Formula 2]

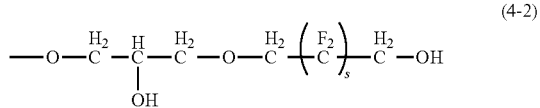 (4-1)

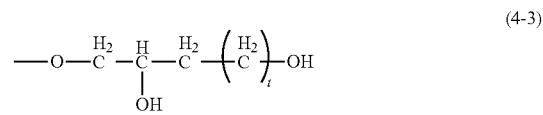 (4-2)

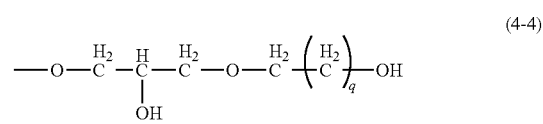 (4-3)

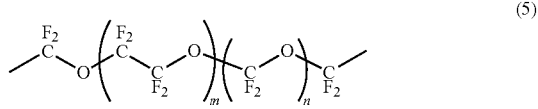 (4-4)

wherein in the formula (4-1), p1 represents an integer of 1 to 2, and p2 represents an integer of 1 to 5;
in the formula (4-2), s represents an integer of 2 to 5;
in the formula (4-3), t represents an integer of 1 to 5; and
in the formula (4-4), q represents an integer of 2 to 5.

[4] The fluorine-containing ether compound according to any one of [1] to [3], wherein $R^3$ in the formula (1) is represented by the following formula (5),

[Chemical Formula 3]

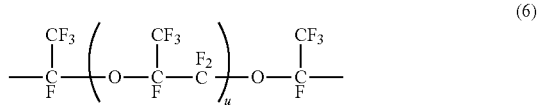 (5)

wherein in the formula (5), m and n indicate an average degree of polymerization,
m represents 1 to 30, and
n represents 0 to 30.

[5] The fluorine-containing ether compound according to any one of [1] to [3], wherein $R^3$ in the formula (1) is represented by the following formula (6) or the following formula (7),

[Chemical Formula 4]

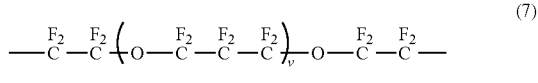 (6)

(7)

wherein in the formula (6), u indicates an average degree of polymerization and represents 1 to 30; and
in the formula (7), v indicates an average degree of polymerization and represents 1 to 30.

[6] The fluorine-containing ether compound according to any one of [1] to [4], wherein the structure of the fluorine-containing ether compound is represented by the following formula (8),

[Chemical Formula 5]

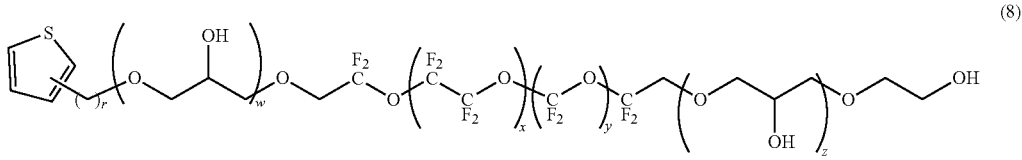

(8)

wherein in the formula (8), x and y indicate an average degree of polymerization, and each represents 1 to 20;

z represents 1 or 2;

w represents 2 or 3; and r represents an integer of 1 to 3.

[7] The fluorine-containing ether compound according to any one of [1] to [6], wherein r represents 2.

[8] The fluorine-containing ether compound according to any one of [1] to [7], wherein a number average molecular weight is in the range of 500 to 10000.

[9] A lubricant for magnetic recording media, comprising the fluorine-containing ether compound according to any one of [1] to [8].

[10] A magnetic recording medium in which at least a magnetic layer, a protective layer, and a lubricant layer are sequentially provided on a substrate, wherein the lubricant layer contains the fluorine-containing ether compound according to any one of [1] to [8].

[11] The magnetic recording medium according to [10], wherein an average film thickness of the lubricant layer is 0.5 nm to 2 nm.

The fluorine-containing ether compound of the present invention is a compound represented by the formula (1), and is suitable as a material for a lubricant for magnetic recording media.

The lubricant for magnetic recording media contains the fluorine-containing ether compound of the present invention. Therefore, even if the thickness of the lubricant layer is thin, the lubricant layer having excellent chemical substance resistance and wear resistance and suppressing surface unevenness can be formed. Therefore, by using the lubricant for magnetic recording media of the present invention, it is possible to further reduce the thickness of the lubricant layer and to contribute to the reduction of the magnetic spacing of the magnetic recording medium provided with the lubricant layer.

The magnetic recording medium of the present invention is provided with a lubricant layer having excellent chemical substance resistance and wear resistance. Therefore, the magnetic recording medium has excellent reliability and durability.

BRIEF DESCRIPTION OF THE DRAWINGS

The FIGURE is a schematic cross-sectional view showing an embodiment of a magnetic recording medium of the present invention.

DETAILED DESCRIPTION OF THE INVENTION

In order to solve the above problem, the present inventors paid attention to the relationship between the molecular structure of the fluorine-containing ether compound contained in the lubricant layer and the protective layer, and carried out intensive research as described below.

The molecular structure of the fluorine-containing ether compound contained in the lubricant layer has a great influence on the film thickness, adhesion characteristics, wear resistance and chemical substance resistance of the lubricant layer.

Conventionally, a perfluoropolyether compound (hereinafter referred to as "PFPE-based compound") containing a polar group such as a hydroxyl group in the molecule is used as a lubricant in order to obtain a lubricant layer having good adhesion properties to a protective layer. However, even in the case of a lubricant layer containing a PFPE-based compound having a plurality of polar groups in the molecule, the adhesion (adherence) of the lubricant layer to the protective layer may not be sufficiently obtained.

As a result of intensive examination by the present inventors, it has been found that, even in a lubricant layer containing a PFPE-based compound having a plurality of polar groups, if the polar groups in the PFPE-based compound are not effectively involved in bonding with an active point on the protective layer, adhesion to the protective layer cannot be sufficiently obtained.

If the adhesion between the lubricant layer and the protective layer is insufficient, the lubricant layer becomes bulky, and it is difficult to obtain a lubricant layer having a uniform film thickness. This is because the PFPE-based compounds contained in the lubricant layer aggregate with each other, or a part of the PFPE-based compound molecules, such as the ends of the molecules, float from the surface of the protective layer, thereby forming unevenness at a molecular level on the surface of the lubricant layer. Further, in a lubricant layer having a large surface unevenness, the film thickness must be sufficiently thick in order to ensure a sufficient coverage rate so as to obtain good chemical substance resistance and wear resistance. Therefore, it is difficult to further reduce the thickness of the lubricant layer by a conventional technique.

Further, as a result of the intensive examination conducted by the present inventors, it has been found that the following tendency is found when a large number of polar groups which are not involved in bonding with the active point on the protective layer exist in the PFPE-based compound contained in the lubricant layer. The chemical substance resistance is insufficient due to easy induction of contamination; or a pickup in which a lubricant adheres to a magnetic head as a foreign substance (smear) is easy to occur.

Therefore, in order to promote the bonding between a plurality of polar groups in the fluorine-containing ether compound and the active site on the protective layer, the present inventors paid attention to the molecular structure of the fluorine-containing ether compound and conducted repeated investigations. As a result, it was found that the fluorine-containing ether compound should satisfy the following (1) to (3).

(1) A suitable flexibility is introduced to the molecular structure of the fluorine-containing ether compound by including a chain structure linked by using an ether bond (—O—).

(2) A suitable distance between each other among a plurality of polar groups contained in the fluorine-containing ether compound is kept.

(3) At least a part of a plurality of polar groups contained in the fluorine-containing ether compound is a hydroxyl group.

Specifically, groups including two or three polar groups are disposed at both a first end and a second end of the perfluoropolyether chain, wherein each polar group is bonded to a different carbon atom, and carbon atoms bonded to the polar group are bonded to one another via a linking group including a carbon atom to which the polar group is not bonded.

Further, in the group arranged at the first end, the polar group is a hydroxyl group, and the linking group has a methylene group (—CH$_2$—) and an ether bond (—O—).

In the lubricant layer containing such a fluorine-containing ether compound, since a plurality of polar groups in the fluorine-containing ether compound contained in the lubricant layer and an active point on the protective layer are easily bonded, the adhesion to the protective layer is good. Therefore, the lubricant layer has a smooth surface in which unevenness is suppressed; a high coverage, a uniform film thickness, and good chemical substance resistance is obtained; and the lubricant layer is unlikely to cause pickup. Therefore, the lubricant layer containing the fluorine-containing ether compound can be further thinned, a touchdown power (TDp) can be increased, and the magnetic spacing can be reduced.

Furthermore, the inventors of the present invention have diligently studied to improve wear resistance of a lubricant layer containing a fluorine-containing ether compound. As a result, it was found that a thiophene alkyl group may be disposed at the end of the first end of the perfluoropolyether chain in the fluorine-containing ether compound.

In the fluorine-containing ether compound, since the thiophene ring contained in the thiophene alkyl group arranged at the end of the first end is a five-membered ring and π-electron rich system, the electron density is higher than, for example, the case where a benzene ring, which is a six-membered ring, is contained. Thus, in the lubricant layer containing the fluorine-containing ether compound, the intermolecular interaction of the thiophene alkyl group and/or the interaction of the thiophene alkyl group with the protective layer becomes strong. As a result, it is estimated that the function of improving wear resistance due to the thiophene ring contained in the thiophene alkyl group can be effectively obtained.

Based on these findings, the present inventors have completed the present invention.

Hereinafter, a fluorine-containing ether compound, a lubricant for a magnetic recording medium (hereinafter referred to as "lubricant" in some cases) and a magnetic recording medium of the present invention will be described in detail. The present invention is not limited to the following embodiments.

[Fluorine-Containing Ether Compound]

The fluorine-containing ether compound of the present embodiment is represented by the following formula (1).

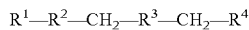 (1)

(In the formula (1), R$^1$ is represented by the following formula (2);

R$^2$ is represented by the following formula (3);

R$^3$ is a perfluoropolyether chain; and

R$^4$ is an organic end group different from R$^1$—R$^2$— and comprises two or three polar groups, wherein each polar group is bonded to a different carbon atom, and the carbon atoms to which the polar groups are bonded are bonded to one another via a linking group containing a carbon atom to which the polar group is not bonded.)

[Chemical Formula 6]

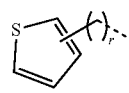 (2)

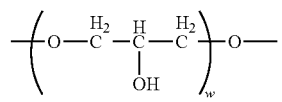 (3)

(In the formula (2), r represents an integer of 1 to 3.)

(In the formula (3), w represents 2 or 3.)

As shown in the formula (1), the fluorine-containing ether compound of the present embodiment has a perfluoropolyether chain represented by R$^3$ (hereinafter referred to as "PFPE chain" in some cases). When a lubricant containing the fluorine-containing ether compound is applied on the protective layer to form a lubricant layer, the PFPE chain covers the surface of the protective layer and imparts lubricity to the lubricant layer to reduce frictional force between the magnetic head and the protective layer.

As shown in the formula (1), a thiophene alkyl group represented by the formula (2) (R$^1$) is disposed at the first end of the PFPE chain through a methylene group and R$^2$ represented by the formula (3). The thiophene alkyl group improves wear resistance in the lubricant layer containing the fluorine-containing ether compound of the present embodiment.

Therefore, the lubricant layer containing the fluorine-containing ether compound of the present embodiment has excellent wear resistance as compared with, for example, a lubricant layer containing a fluorine-containing ether compound in which a hydroxyl group is arranged instead of a thiophene alkyl group.

In the fluorine-containing ether compound represented by the formula (1), the alkylene group in the thiophene alkyl group represented by the formula (2) (R$^1$) is a group selected from the group consisting of a methylene group, an ethylene group and a propylene group. The alkylene group in R$^1$ can be appropriately selected according to the performance required for a lubricant containing a fluorine-containing ether compound. When the alkylene group is an ethylene group or a propylene group, the fluorine-containing ether compound has higher stability to an acid base as compared with the case where the alkylene group is a methylene group. Therefore, the alkylene group is preferably an ethylene group or a propylene group. In the fluorine-containing ether compound represented by the formula (1), the distance between the thiophene ring and R$^2$ is close because r in the formula (2) is 3 or less. Therefore, in the lubricant layer containing the fluorine-containing ether compound, the effect of improving adhesion to the protective layer is sufficiently obtained by the hydroxyl group contained in R$^2$.

As a result, the thiophene alkyl group in the fluorine-containing ether compound and the protective layer are easily brought close to each other, and the effect of improving wear resistance by the thiophene alkyl group is effectively obtained. The alkylene group is most preferably an ethylene group (In the formula (2), r is 2.) because the fluorine-containing ether compound has high stability and can form a lubricant layer excellent in wear resistance.

The alkylene group may be bonded to the 2-position or 3-position of the thiophene ring of the thiophene alkyl group.

$R^2$, which is bonded to the first end of the PFPE chain represented by $R^3$, is a divalent linking group having a repeating number of 2 or 3. $R^2$ contains 2 or 3 hydroxyl groups (—OH) as shown in the formula (3). In $R^2$, 2 or 3 carbon atoms to which a hydroxyl group is bonded are bonded through a linking group consisting of a methylene group (—$CH_2$—) and an ether bond (—O—). Therefore, the distance between the two or three hydroxyl groups contained in $R^2$ is appropriate. Further, $R^2$ has an ethereal oxygen atom at both ends of the repeating unit as shown in the formula (3). Thus, $R^2$ imparts appropriate flexibility to the molecular structure of the fluorine-containing ether compound represented by the formula (1). Therefore, when the lubricant layer containing the fluorine-containing ether compound of the present embodiment is formed on the protective layer, two or three hydroxyl groups in $R^2$ are likely to participate in bonding between the active point on the protective layer and the lubricant layer. Therefore, the lubricant layer containing the fluorine-containing ether compound of the present embodiment has excellent adhesion (adherence) to the protective layer.

In the fluorine-containing ether compound represented by the formula (1), $R^2$ is a linking group represented by the formula (3), and in the formula (3), w represents 2 or 3. When w is 2 or 3 in the formula (3), the number of hydroxyl groups in the linking group represented by the formula (3) is appropriate, and the lubricant containing the fluorine-containing ether compound can form a lubricant layer which is excellent in adhesion to the protective layer and has a high coverage. In the formula (3), w is preferably 2. Further, when w is 2 or 3 in the formula (3), the polarity of the fluorine-containing ether compound does not become too high by having too many hydroxyl groups. Therefore, it is possible to prevent the lubricant layer containing the fluorine-containing ether compound from adhering to the magnetic head as a foreign substance (smear) due to the polarity of the fluorine-containing ether compound being too high; and pickup can be suppressed.

In addition, at an end (the second end), opposite to $R^2$, of the PFPE chain represented by $R^3$ of formula (1), an organic end group represented by $R^4$ is arranged via a methylene group. The organic end group represented by $R^4$ includes two or three polar groups. The two or three polar groups contained in the organic end group represented by $R^4$ bring the lubricant layer and the protective layer into close contact with each other in the lubricant layer containing the fluorine-containing ether compound of the present embodiment, thereby improving chemical substance resistance and wear resistance, and suppressing pickup.

The two or three polar groups contained in the organic end group represented by $R^4$ are bonded to different carbon atoms, and the carbon atoms to which the polar groups are bonded are bonded through a linking group containing a carbon atom to which the polar group is not bonded. Therefore, the two or three polar groups contained in $R^4$ have an appropriate distance between the polar groups. As a result, the fluorine-containing ether compound having the end group represented by $R^4$ is less likely to aggregate than, for example, a fluorine ether compound in which at least a part of the carbon atoms to which the polar groups contained in the end group represented by $R^4$ is bonded. Therefore, in the lubricant layer containing the fluorine-containing ether compound represented by the formula (1), it is possible to prevent the fluorine-containing ether compound which exists without adhering (adsorbing) to the protective layer from aggregating and adhering to the magnetic head as a foreign substance (smear), thereby suppressing pickup. Further, since the fluorine-containing ether compounds are unlikely to aggregate with each other, the fluorine-containing ether compounds in the lubricant layer are easily arranged in a state in which they are spread in the surface direction and uniformly extended on the protective layer. From this, it is presumed that the lubricant containing the fluorine-containing ether compound of the present embodiment can cover the surface of the protective layer with a high coverage even if it is thin, and can form a lubricant layer having excellent chemical substance resistance and wear resistance. Therefore, the lubricant containing the fluorine-containing ether compound of the present embodiment contributes to thinning of the lubricant layer (reduction of magnetic spacing).

In the fluorine-containing ether compound represented by the formula (1), $R^4$ is an end group different from $R^1$—$R^2$. The organic end group represented by $R^4$ contributes to adhesion between the protective layer to which the lubricant containing the fluorine-containing ether compound of the present embodiment is applied and the lubricant layer formed by applying the lubricant. Since the number of polar groups contained in $R^4$ is two or three, the lubricant containing the fluorine-containing ether compound has excellent adhesion to the protective layer and can form the lubricant layer having a high coverage. The number of polar groups contained in $R^4$ is preferably three. If the number of polar groups contained in $R^4$ is too large, the polarity of the fluorine-containing ether compound becomes too high, and pickup in which the lubricant layer containing the fluorine-containing ether compound adheres to the magnetic head as a foreign substance (smear) tends to occur. In the present embodiment, the number of polar groups contained in $R^4$ is two or three. Therefore, the occurrence of pickup, due to the polarity of the fluorine-containing ether compound being too high, can be suppressed.

$R^4$ in the formula (1) can be appropriately selected according to the performance required for a lubricant containing a fluorine-containing ether compound.

Examples of the polar groups in $R^4$ include a hydroxyl group (—OH), an amino group (—$NH_2$), a carboxyl group (—COOH), and a mercapto group (—SH). The ether bond (—O—) is not included in the polar groups in $R^4$. Among the above polar groups, the hydroxyl group is preferable. The two or three polar groups contained in the organic end group represented by $R^4$ may be a combination of different polar groups, but all of them are preferably hydroxyl groups. The hydroxyl group has a large interaction with the protective layer, especially the protective layer formed of a carbon-based material. Therefore, when all of the polar groups are hydroxyl groups, the lubricant layer containing the fluorine-containing ether compound has high adhesion to the protective layer.

In the formula (1), $R^4$ is preferably an end group represented by any one of the following formulae (4-1) to (4-4). Such $R^4$ contributes to high adhesion and coverage between the protective layer to which the lubricant containing the fluorine-containing ether compound of the present embodiment is applied and the lubricant layer formed by applying the lubricant.

[Chemical Formula 7]

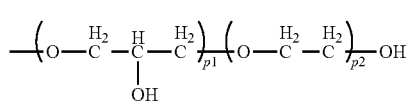

(4-1)

(In the formula (4-1), p1 represents an integer of 1 to 2, and p2 represents an integer of 1 to 5.)

In the formula (4-1), p1 is an integer of 1 to 2, and is preferably 2.

In the formula (4-1), p2 is an integer of 1 to 5. When p2 is an integer of 1 to 5, the distance between hydroxyl groups in the end group represented by the formula (4-1) is appropriate. Therefore, when p2 is an integer of 1 to 5, the fluorine-containing ether compound has excellent adhesion to the protective layer and can form a lubricant layer having a high coverage. From the viewpoint of adhesion to the protective layer, p2 is preferably 1 to 2, and most preferably 1.

[Chemical Formula 8]

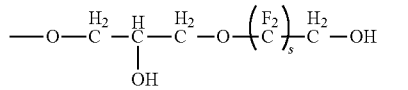

(4-2)

(In the formula (4-2), s represents an integer of 2 to 5.)

In the formula (4-2), s is an integer of 2 to 5. In this case, the distance between the hydroxyl group on the $R^3$ side and the hydroxyl group at the end is appropriate. Therefore, when s is an integer of 2 to 5, the fluorine-containing ether compound has excellent adhesion to the protective layer and can form a lubricant layer having a high coverage. From the viewpoint of adhesion to the protective layer, s is preferably 2 or 3, and most preferably 2.

[Chemical Formula 9]

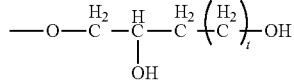

(4-3)

(In the formula (4-3), t represents an integer of 1 to 5.)

In the formula (4-3), t is an integer of 1 to 5. In this case, the distance between the hydroxyl group on the $R^3$ side and the hydroxyl group at the end is appropriate. Therefore, when t is an integer of 1 to 5, the fluorine-containing ether compound has excellent adhesion to the protective layer and can form a lubricant layer having a high coverage. From the viewpoint of adhesion to the protective layer, t is preferably 1 or 2, and most preferably 1.

[Chemical Formula 10]

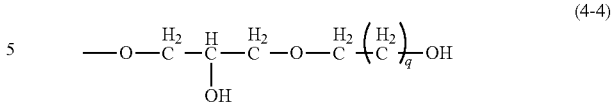

(4-4)

(In the formula (4-4), q represents an integer of 2 to 5.)

In the formula (4-4), q is an integer of 2 to 5. In this case, the distance between the hydroxyl group on the $R^3$ side and the hydroxyl group at the end is appropriate. Therefore, when q is an integer of 2 to 5, the fluorine-containing ether compound has excellent adhesion to the protective layer and can form a lubricant layer having a high coverage. From the viewpoint of adhesion to the protective layer, q is preferably 2 or 3, and most preferably 2.

The fluorine-containing ether compound of the present embodiment, represented by the formula (1), is an asymmetric compound in which different end groups ($R^1$—$R^2$—, —$R^4$) are respectively bonded to both ends of the PFPE chain ($R^3$). The compound, in which different end groups are bonded to both ends of the PFPE chain, respectively, can provide superior chemical substance resistance and wear resistance compared to compounds in which the same end groups are bonded to both ends of the PFPE chain, because of the synergistic effect of groups ($R^1$—$R^2$—, —$R^4$) having different functions which are bonded at the molecular ends, respectively.

In particular, in the fluorine-containing ether compound of the present embodiment, the thiophene alkyl group represented by $R^1$ is bonded to $R^2$ containing 2 or 3 hydroxyl groups (—OH). Therefore, in the lubricant layer containing the fluorine-containing ether compound of the present embodiment, the thiophene alkyl group and the protective layer are easily brought into close contact due to an effect of improving the adhesion to the protective layer by the hydroxyl group contained in $R^2$. Therefore, in the lubricant layer containing the fluorine-containing ether compound of the present embodiment, the function of improving the wear resistance by the thiophene alkyl group effectively works.

In the fluorine-containing ether compound of the present embodiment, 2 or 3 hydroxyl groups, which are arranged at a proper distance and contained in $R^2$, and 2 or 3 polar groups, which are arranged at a proper distance and contained in $R^4$, are arranged at both ends of $R^3$ with a good balance via methylene groups (—$CH_2$—), respectively. Therefore, the lubricant layer containing the fluorine-containing ether compound of the present embodiment has excellent adhesion (adherence) to the protective layer, and can coat the surface of the protective layer with a high coverage. Therefore, the lubricant layer containing the fluorine-containing ether compound of the present embodiment has good wear resistance and chemical substance resistance, can be further thinned, and can contribute to the reduction of magnetic spacing in the magnetic recording medium.

In the formula (1), $R^3$ is a perfluoropolyether chain (PFPE chain). $R^3$ is not particularly limited, and can be appropriately selected according to the performance required for a lubricant containing a fluorine-containing ether compound.

In the formula (1), $R^3$ is preferably a PFPE chain represented by the following formula (5). When $R^3$ is a PFPE chain represented by the formula (5), the synthesis of the fluorine-containing ether compound is easy and preferable.

[Chemical Formula 11]

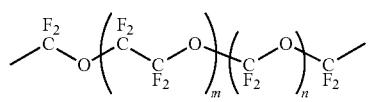
(5)

(In the formula (5), m and n indicate an average degree of polymerization, m represents 1 to 30, and n represents 0 to 30.)

In the formula (5), there is no particular restriction on the sequence order of the repeating units ($CF_2$—$CF_2$—O) and ($CF_2$—O). In the formula (5), the number m of ($CF_2$—$CF_2$—O) indicating an average degree of polymerization and the number n of ($CF_2$—O) indicating an average degree of polymerization may be the same or different. The formula (5) may include any one of a random copolymer, a block copolymer and an alternating copolymer, all of which contain monomer units ($CF_2$—$CF_2$—O) and ($CF_2$—O).

When $R^3$ in the formula (1) is the formula (5), m indicating an average degree of polymerization is 1 to 30, preferably 1 to 20, and more preferably 1 to 15. When $R^3$ in the formula (1) is the formula (5), n indicating an average degree of polymerization is 0 to 30, preferably 1 to 20, and more preferably 1 to 15. When n is 0, m is preferably 1 to 17.

In the formula (1), $R^3$ may be represented by the following formula (6) or formula (7).

[Chemical Formula 12]

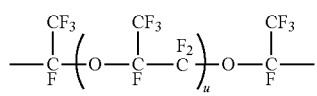
(6)

(In the formula (6), u indicates an average degree of polymerization and represents 1 to 30.)

In the formula (6), when u is 1 to 30, the number average molecular weight of the fluorine-containing ether compound of the present embodiment tends to be in a preferable range. u is preferably 3 to 20, and more preferably 4 to 10.

[Chemical Formula 13]

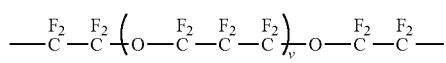
(7)

(In the formula (7), v indicates an average degree of polymerization and represents 1 to 30.)

In the formula (7), when v is 1 to 30, the number average molecular weight of the fluorine-containing ether compound of the present embodiment tends to be in a preferable range. v is preferably 3 to 20, and more preferably 4 to 10.

When $R^3$ in the formula (1) is represented by any one of formulae (5) to (7), the synthesis of the fluorine-containing ether compound is easy, and therefore, such $R^3$ is preferable. When $R^3$ in the formula (1) is represented by any one of formulae (5) to (7), the ratio of the number of oxygen atoms (number of ether bonds (—O—)) to the number of carbon atoms in the perfluoropolyether chain, and the arrangement of the oxygen atoms in the perfluoropolyether chain are appropriate. Therefore, the fluorine-containing ether compound has a proper hardness. Therefore, the fluorine-containing ether compound applied on the protective layer is unlikely to aggregate on the protective layer, and a much thinner lubricant layer can be formed with a sufficient coverage.

In particular, when $R^3$ in the formula (1) is represented by the formula (5), it is more preferable because the raw material can be easily obtained.

The fluorine-containing ether compound represented by the formula (1) is preferably a compound represented by the following formula (8). The fluorine-containing ether compound represented by the formula (8) can be easily synthesized since the raw material is readily available.

[Chemical Formula 14]

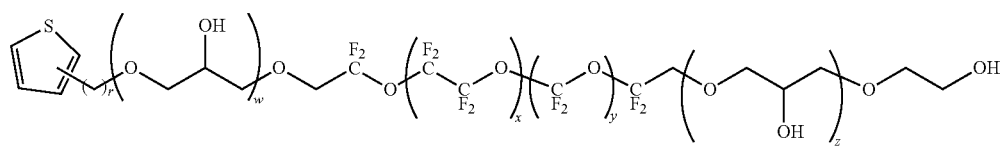
(8)

(In the formula (8), x and y indicate an average degree of polymerization, and each represents 1 to 20. z represents 1 or 2. w represents 2 or 3. r represents 1 to 3.)

In the formula (8), x and y indicating an average degree of polymerization are each 1 to 20, and preferably 1 to 15.

In the formula (8), z represents 1 or 2, and preferably represents 2.

In the formula (8), w represents 2 or 3, and preferably represents 2.

The alkylene group in the thiophene alkyl group in the formula (8) is an alkylene group selected from the group consisting of a methylene group, an ethylene group and a propylene group, and is preferably an ethylene group. The alkylene group in the thiophene alkyl group may be bonded to the 2-position or 3-position of the thiophene ring of the thiophene alkyl group.

Specifically, the fluorine-containing ether compound represented by the formula (1) is preferably any one of compounds represented by the following formulae (A) to (L). The number of repetitions indicated by m and n in formulae (A) to (L) is a value indicating an average value, and therefore is not necessarily an integer.

All of the compounds represented by the formulae (A) to (E) have $R^1$ represented by the formula (2). $R^2$ is represented by the formula (3), and w in $R^2$ is 2. $R^3$ is the formula (5). $R^4$ is the formula (4-1), p1 in the formula (4-1) is 1, and p2 is 1.

In the compound represented by the formula (A), the alkylene group in $R^1$ is a methylene group, and is bonded to the 2-position of the thiophene ring of $R^1$.

In the compound represented by the formula (B), the alkylene group in $R^1$ is an ethylene group and is bonded to the 2-position of the thiophene ring of $R^1$.

In the compound represented by the formula (C), the alkylene group in $R^1$ is a propylene group and is bonded to the 2-position of the thiophene ring of $R^1$.

In the compound represented by the formula (D), the alkylene group in $R^1$ is a methylene group, and is bonded to the 3-position of the thiophene ring of $R^1$.

In the compound represented by the formula (E), the alkylene group in $R^1$ is an ethylene group and is bonded to the 3-position of the thiophene ring of $R^1$.

In the compounds represented by the formula (F) and (G), $R^1$ is represented by the formula (2), the alkylene group in $R^1$ is an ethylene group and is bonded to the 2-position of the thiophene ring of R'. $R^2$ is represented by the formula (3). $R^3$ is the formula (5). $R^4$ is the formula (4-1), p1 in the formula (4-1) is 2, and p2 is 1.

In the compound represented by the formula (F), w in $R^2$ is 2.

In the compound represented by the formula (G), w in $R^2$ is 3.

In each of the compounds represented by the formulae (H) to (J), $R^1$ is represented by the formula (2), the alkylene group in $R^1$ is an ethylene group and is bonded to the 2-position of the thiophene ring of R'. $R^2$ is represented by the formula (3), and w in $R^2$ is 2. $R^3$ is the formula (5).

In the compound represented by the formula (H), $R^4$ is represented by the formula (4-4), and q in the formula (4-4) is 2.

In the compound represented by the formula (I), $R^4$ is represented by the formula (4-2), and s in the formula (4-2) is 2.

In the compound represented by the formula (J), $R^4$ is represented by the formula (4-3), and t in the formula (4-3) is 1.

In each of the compounds represented by the formula (K) and formula (L), $R^1$— is represented by the formula (2), the alkylene group in $R^1$— is an ethylene group and is bonded to the 2-position of the thiophene ring of $R^2$ is represented by the formula (3), and w in $R^2$ is 2. $R^4$ is the formula (4-1), p1 in the formula (4-1) is 1, and p2 is 1. In the compound represented by the formula (K), $R^3$ is the formula (7).

In the compound represented by the formula (L), $R^3$ is the formula (5) and n is 0.

[Chemical Formula 15]

(A)

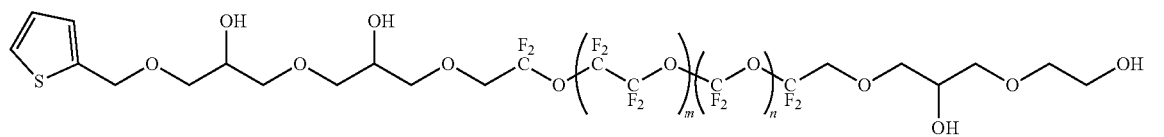

(B)

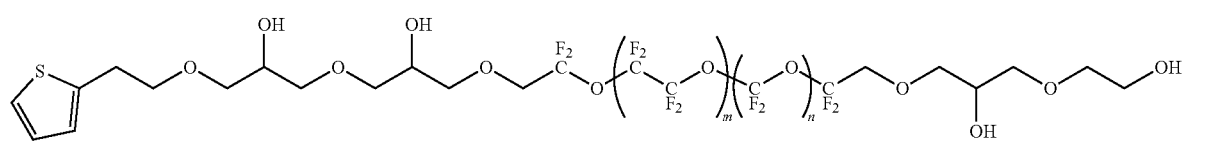

(C)

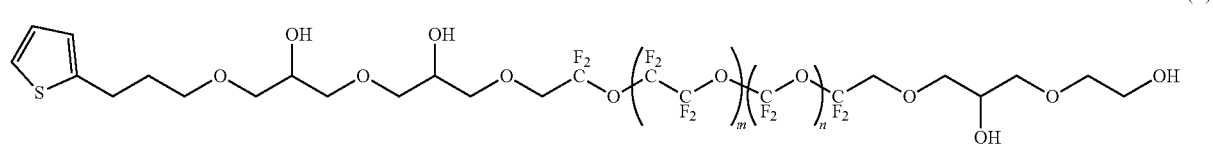

(D)

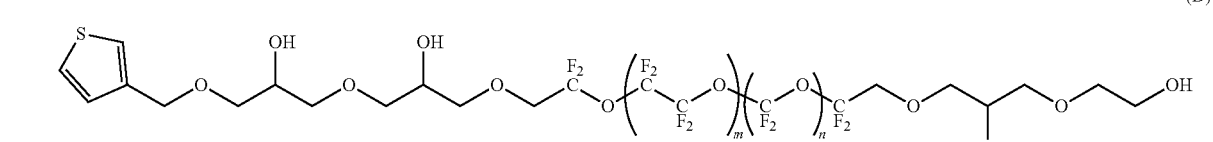

(E)

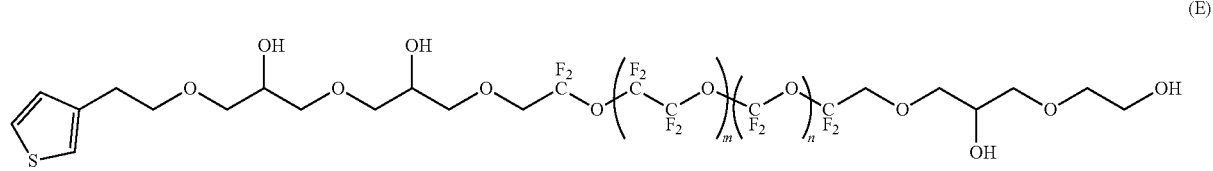

(F)

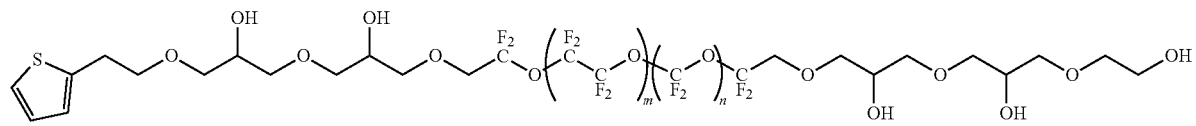

(In the formula (A), m and n indicate an average degree of polymerization, m is 1 to 30, and n is 1 to 30.)

(In the formula (B), m and n indicate an average degree of polymerization, m is 1 to 20, and n is 1 to 20.) (In the formula (C), m and n indicate an average degree of polymerization, m is 1 to 20, and n is 1 to 20.)

(In the formula (D), m and n indicate an average degree of polymerization, m is 1 to 20, and n is 1 to 20.) (In the formula (E), m and n indicate an average degree of polymerization, m is 1 to 20, and n is 1 to 20.)

(In the formula (F), m and n indicate an average degree of polymerization, m is 1 to 20, and n is 1 to 20.)

(In the formula (I), m and n indicate an average degree of polymerization, m is 1 to 20, and n is 1 to 20.)

(In the formula (J), m and n indicate an average degree of polymerization, m is 1 to 20, and n is 1 to 20.) (In the formula (K), v indicates an average degree of polymerization, and v is 1 to 20.)

(In the formula (L), m indicates an average degree of polymerization, and m is 1 to 20.)

When the compound represented by the formula (1) is any one of the compounds represented by the formulae (A) to (L), the raw material is readily available. In addition, any one of the compounds represented by the formulae (A) to (L)

[Chemical Formula 16]

(G)

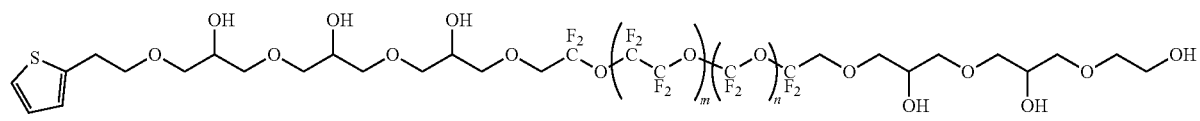

(H)

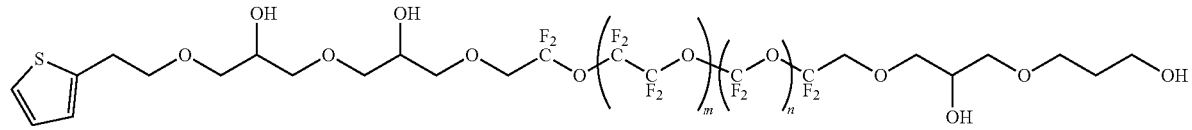

(I)

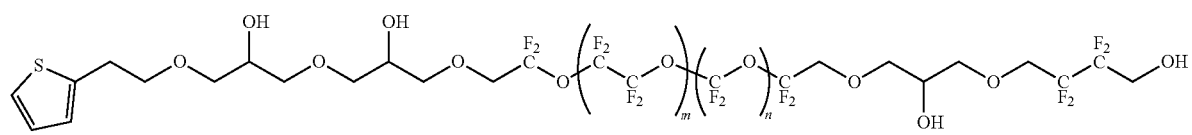

(J)

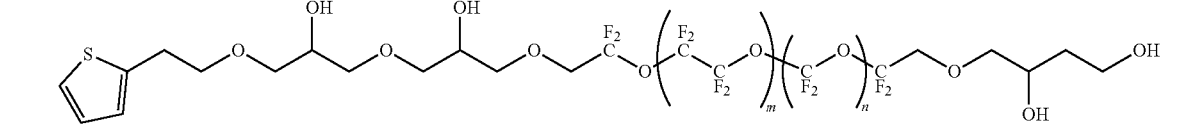

(K)

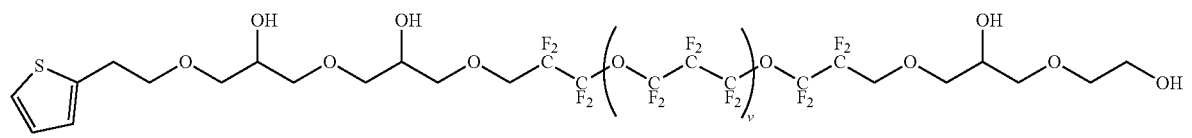

(L)

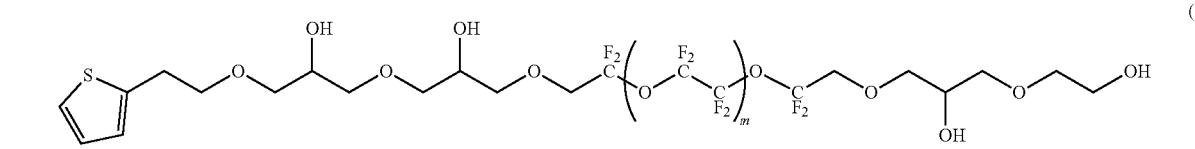

(In the formula (G), m and n indicate an average degree of polymerization, m is 1 to 20, and n is 1 to 20.)

(In the formula (H), m and n indicate an average degree of polymerization, m is 1 to 20, and n is 1 to 20.)

is preferable because even if the thickness of the lubricant layer is thin, it is possible to form a lubricant layer that provides further excellent chemical substance resistance and wear resistance.

The number average molecular weight (Mn) of the fluorine-containing ether compound of the present embodiment is preferably within the range of 500 to 10000, more preferably within the range of 700 to 7000, and particularly preferably within the range of 800 to 4000. When the number average molecular weight is 500 or more, the lubricant containing the fluorine-containing ether compound of the present embodiment is unlikely to evaporate. Therefore, when the number average molecular weight is 500 or more, the lubricant can be prevented from being evaporated and transferred to the magnetic head. When the number average molecular weight is 10,000 or less, the viscosity of the fluorine-containing ether compound is appropriate. Therefore, when the number average molecular weight is 10,000 or less, a thin lubricant layer can be easily formed by applying a lubricant containing the fluorine-containing ether compound. The number average molecular weight of the fluorine-containing ether compound is more preferably 4000 or less, because it has a viscosity that is easy to handle when applied to a lubricant.

The number average molecular weight (Mn) of the fluorine-containing ether compound is a value measured by $^1$H-NMR and $^{19}$F-NMR by using AVANCE 111-400 manufactured by Bruker BioSpin. Specifically, the number of repeating units of the PFPE chain is calculated from the integral value measured by $^{19}$F-NMR, and then the number average molecular weight is calculated. In NMR (nuclear magnetic resonance) measurement, the sample is diluted in deuterated acetone solvent (hexafluorobenzene is added as a reference substance) and is used for measurement. The standard of $^{19}$F-NMR chemical shift was set to −164.7 ppm for the peak of hexafluorobenzene. The standard of $^1$H-NMR chemical shift was set to 2.05 ppm for the peak of acetone.

"Production Method"

The method for producing the fluorine-containing ether compound of the present embodiment is not particularly limited, and the fluorine-containing ether compound can be produced using a conventionally known production method. The fluorine-containing ether compound of the present embodiment can be produced using the method shown below, for example.

First, a fluorine-based compound having a perfluoropolyether main chain corresponding to $R^3$ in the formula (1) and having hydroxymethyl groups (—CH$_2$OH) arranged at both ends of the molecule is prepared.

Next, a hydroxyl group of the hydroxymethyl group disposed at one end of the fluorine-based compound is substituted with a group consisting of $R^1$—$R^2$— in the formula (1) (a first reaction). Thereafter, a hydroxy group of the hydroxymethyl group arranged at the other end is substituted with the end group consisting of —$R^4$ in the formula (1) (a second reaction).

The first reaction and the second reaction can be carried out by a conventionally known method, and can be appropriately determined according to the types or the like of $R^1$, $R^2$, or $R^4$ in the formula (1). Either of the first reaction and the second reaction may be carried out first.

The fluorine-containing ether compound of the present embodiment is a compound represented by the formula (1). Therefore, when the lubricant containing the compound is used to form the lubricant layer on the protective layer, the surface of the protective layer is covered with the PFPE chain represented by $R^3$ in the formula (1). At the same time, the frictional force between the magnetic head and the protective layer is reduced. In the lubricant layer formed by using the lubricant containing the fluorine-containing ether compound of the present embodiment, excellent wear resistance can be obtained by the intermolecular interaction of the thiophene alkyl groups represented by $R^1$ and/or the interaction of the thiophene alkyl group with the protective layer.

The lubricant containing the fluorine-containing ether compound of the present embodiment adheres to the protective layer by bonding the two or three hydroxyl groups contained in the linking group represented by $R^2$ with the protective layer. At the same time, the lubricant adheres to the protective layer by bonding the two or three polar groups contained in the end group represented by $R^4$ with the protective layer.

In the lubricant containing the fluorine-containing ether compound of the present embodiment, 2 or 3 hydroxyl groups contained in the linking group represented by $R^2$ are bonded to different carbon atoms, and the carbon atoms to which the hydroxyl groups are bonded are bonded to one another via a linking group consisting of a methylene group (—CH$_2$—) and an ether bond (—O—). In addition, two or three polar groups contained in the end group represented by $R^4$ are bonded to different carbon atoms, and the carbon atoms to which the polar groups are bonded are bonded to one another via a linking group containing a carbon atom to which the polar group is not bonded. Therefore, in the lubricant containing the fluorine-containing ether compound of the present embodiment, a plurality of polar groups in the fluorine-containing ether compound and the active point on the protective layer are easily bonded to each other, the fluorine-containing ether compounds are unlikely to aggregate, and the surface of the protective layer can be coated with a high coverage even if the thickness is thin.

[Lubricant for Magnetic Recording Media]

The lubricant for magnetic recording medium of the present embodiment contains a fluorine-containing ether compound represented by the formula (1).

The lubricant of the present embodiment may use one or more known materials as a lubricant material by mixing them as necessary, as long as the known material does not impair the characteristics obtained by containing the fluorine-containing ether compound represented by the formula (1).

Specific examples of known materials include, for example, FOMBLIN (registered trademark) ZDIAC, FOMBLIN ZDEAL, FOMBLIN AM-2001 (the above materials are manufactured by Solvay Solexis), Moresco A20H (manufactured by Moresco) and the like. The known material used in combination with the lubricant of the present embodiment preferably has a number average molecular weight of 1000 to 10,000.

When the lubricant of the present embodiment contains materials other than the fluorine-containing ether compound represented by the formula (1), the amount of the fluorine-containing ether compound represented by the formula (1) in the lubricant of the present embodiment is preferably 50% by mass or more, and more preferably 70% by mass or more. The amount of the fluorine-containing ether compound represented by the formula (1) may be 80% by mass or more or 90% by mass or more.

Since the lubricant of the present embodiment contains the fluorine-containing ether compound represented by the formula (1), the surface of the protective layer can be coated with a high coverage rate even when the thickness is reduced. As a result, a lubricant layer having excellent chemical substance resistance and wear resistance and having suppressed surface unevenness can be obtained.

[Magnetic Recording Medium]

The magnetic recording medium of the present embodiment is obtained by providing at least a magnetic layer, a protective layer, and a lubricant layer sequentially on a substrate.

In the magnetic recording medium of the present embodiment, one or more base layers can be provided between the substrate and the magnetic layer as necessary. Further, an adhesion layer and/or a soft magnetic layer can be provided between the base layer and the substrate.

The FIGURE is a schematic cross-sectional view showing an embodiment of the magnetic recording medium of the present invention.

The magnetic recording medium 10 of the present embodiment has a structure in which an adhesion layer 12, a soft magnetic layer 13, a first base layer 14, a second base layer 15, a magnetic layer 16, a protective layer 17 and a lubricant layer 18 are sequentially provided on a substrate 11.

"Substrate"

As the substrate 11, for example, a nonmagnetic substrate in which a film made of NiP or NiP alloy is formed on a base made of a metal or alloy material such as Al or Al alloy can be used.

As the substrate 11, a nonmagnetic substrate made of a nonmetallic material such as glass, ceramics, silicon, silicon carbide, carbon, or resin, or a nonmagnetic substrate obtained by forming a film made of NiP or NiP alloy on a base made of these nonmetallic materials, may be used.

The glass substrate is suitable for increasing the recording density because it has rigidity and excellent smoothness. Examples of the glass substrates include an aluminosilicate glass substrate, and a chemically strengthened aluminosilicate glass substrate is particularly preferable.

The roughness of the main surface of the substrate 11 is preferably ultra-smooth with Rmax of 6 nm or less and Ra of 0.6 nm or less. Here, the surface roughness Rmax and Ra are based on the standards of JIS B0601.

"Adhesion Layer"

The adhesion layer 12 prevents the progress of corrosion of the substrate 11 that occurs when the substrate 11 and the soft magnetic layer 13 provided on the adhesion layer 12 are disposed in contact with each other.

The material of the adhesion layer 12 may be appropriately selected from, for example, Cr, Cr alloy, Ti, Ti alloy, CrTi, NiAl, AlRu alloy and the like. The adhesion layer 12 can be formed by, for example, a sputtering method.

"Soft magnetic Layer"

The soft magnetic layer 13 preferably has a structure in which a first soft magnetic film, an intermediate layer made of a Ru film, and a second soft magnetic film are sequentially stacked. That is, it is preferable that the soft magnetic layer 13 has a structure in which the soft magnetic films above and below the intermediate layer are linked by antiferromagnetic coupling (AFC) by sandwiching the intermediate layer made of a Ru film between the two soft magnetic films.

Examples of the material of the first soft magnetic film and the second soft magnetic film include a CoZrTa alloy and a CoFe alloy.

It is preferable to add any one of Zr, Ta, and Nb to the CoFe alloy used for the first soft magnetic film and the second soft magnetic film. This promotes the amorphization of the first soft magnetic film and the second soft magnetic film, and as a result, it becomes possible to improve the orientation of the first base layer (seed layer). At the same time, it becomes possible to reduce the floating height of the magnetic head.

The soft magnetic layer 13 can be formed by, for example, a sputtering method.

"First Base Layer"

The first base layer 14 is a layer for controlling the orientation and crystal sizes of the second base layer 15 and the magnetic layer 16 provided on top of the first base layer 14.

Examples of the first base layer 14 include a Cr layer, a Ta layer, a Ru layer, a CrMo alloy layer, a CoW alloy layer, a CrW alloy layer, a CrV alloy layer, and a CrTi alloy layer.

The first base layer 14 can be formed by, for example, a sputtering method.

"Second Base Layer"

The second base layer 15 is a layer for turning the magnetic layer 16 to a more favorable orientation. The second base layer 15 is preferably a layer made of Ru or a Ru alloy.

The second base layer 15 may be composed of a single layer or may be composed of a plurality of layers. When the second base layer 15 is composed of a plurality of layers, all the layers may be formed from the same material, or at least one layer may be formed from a different material.

The second base layer 15 can be formed by, for example, a sputtering method.

"Magnetic Layer"

The magnetic layer 16 is made of a magnetic film whose easy magnetization axis is oriented perpendicularly or horizontally to the substrate surface. The magnetic layer 16 is a layer containing Co and Pt, and may be a layer containing an oxide, Cr, B, Cu, Ta, Zr or the like in order to further improve the SNR characteristics.

Examples of the oxide contained in the magnetic layer 16 include $SiO_2$, SiO, $Cr_2O_3$, CoO, $Ta_2O_3$, and $TiO_2$.

The magnetic layer 16 may be composed of one layer, or may be composed of a plurality of magnetic layers made of materials having different compositions.

For example, when the magnetic layer 16 is composed of three layers of a first magnetic layer, a second magnetic layer, and a third magnetic layer that are stacked in order from the bottom, it is preferable that the first magnetic layer has a granular structure that includes a material containing Co, Cr, and Pt and further containing an oxide. As the oxide contained in the first magnetic layer, for example, an oxide of each Cr, Si, Ta, Al, Ti, Mg, Co, and the like is preferably used. Among these, $TiO_2$, $Cr_2O_3$, $SiO_2$ or the like can be preferably used. The first magnetic layer is preferably made of a composite oxide in which two or more types of oxides are added. Of these, $Cr_2O_3$—$SO_2$, $Cr_2O_3$—$TiO_2$, $SiO_2$—$TiO_2$ or the like can be preferably used.

The first magnetic layer may include at least one element selected from B, Ta, Mo, Cu, Nd, W, Nb, Sm, Tb, Ru, and Re in addition to Co, Cr, Pt, and an oxide.

The same material as those used for the first magnetic layer can be used for the second magnetic layer. The second magnetic layer preferably has a granular structure.

The third magnetic layer preferably has a non-granular structure made of a material containing Co, Cr, and Pt, but containing no oxide. The third magnetic layer may contain one or more elements selected from B, Ta, Mo, Cu, Nd, W, Nb, Sm, Tb, Ru, Re, and Mn in addition to Co, Cr, and Pt.

When the magnetic layer 16 is formed of a plurality of magnetic layers, it is preferable to provide a nonmagnetic layer between adjacent magnetic layers. When the magnetic layer 16 is composed of three layers of the first magnetic layer, the second magnetic layer, and the third magnetic layer, it is preferable to provide a nonmagnetic layer between the first magnetic layer and the second magnetic layer, and between the second magnetic layer and the third magnetic layer.

Examples of materials that can be used favorably for the non-magnetic layers provided between the adjacent magnetic layers of the magnetic layer 16 include Ru, a Ru alloy, a CoCr alloy, and a CoCrX1 alloy (wherein X1 represents one or more elements selected from among Pt, Ta, Zr, Re, Ru, Cu, Nb, Ni, Mn, Ge, Si, O, N, W, Mo, Ti, V and B), and the like.

It is preferable to use an alloy material containing an oxide, a metal nitride, or a metal carbide for the nonmagnetic layer provided between the adjacent magnetic layers of the magnetic layer 16. Specific examples of oxides that may be used include $SiO_2$, $Al_2O_3$, $Ta_2O_5$, $Cr_2O_3$, MgO, $Y_2O_3$, $TiO_2$, and the like. Examples of metal nitrides that may be used include AlN, $Si_3N_4$, TaN, CrN, and the like. Examples of metal carbides that may be used include TaC, BC, SiC, and the like.

The nonmagnetic layer can be formed by, for example, a sputtering method.

The magnetic layer 16 is preferably a magnetic layer for perpendicular magnetic recording, in which the easy magnetization axis is oriented in a direction perpendicular to the substrate surface in order to achieve a higher recording density. The magnetic layer 16 may be in-plane magnetic recording.

The magnetic layer 16 may be formed by using any conventionally known method such as a vapor deposition method, an ion beam sputtering method, or a magnetron sputtering method. The magnetic layer 16 is usually formed by a sputtering method.

"Protective Layer"

The protective layer 17 protects the magnetic layer 16. The protective layer 17 may be composed of one layer or may be composed of a plurality of layers. Examples of the material of the protective layer 17 include carbon, carbon containing nitrogen, and silicon carbide.

As the protective layer 17, a carbon-based protective layer can be preferably used, and an amorphous carbon protective layer is particularly preferable. It is preferable that the protective layer 17 is a carbon-based protective layer because interaction with a polar group (particularly a hydroxy group) contained in the fluorine-containing ether compound in the lubricant layer 18 is further increased.

The adhesion between the carbon-based protective layer and the lubricant layer 18 can be controlled by making the carbon-based protective layer to contain hydrogenated carbon and/or nitrogenated carbon, and then adjusting the hydrogen content and/or the nitrogen content in the carbon-based protective layer. The hydrogen content in the carbon-based protective layer is preferably 3 to 20 atomic % as measured by the hydrogen forward scattering method (HFS). The nitrogen content in the carbon-based protective layer is preferably 4 to 12 atomic % as measured by X-ray photoelectron spectroscopy (XPS).

The hydrogen and/or nitrogen contained in the carbon-based protective layer need not be uniformly contained in the entire carbon-based protective layer. For example, the carbon-based protective layer is preferably a composition gradient layer in which nitrogen is contained on the lubricant layer 18 side of the protective layer 17 and hydrogen is contained on the magnetic layer 16 side of the protective layer 17. In this case, the adhesion between the magnetic layer 16 and the carbon-based protective layer and the adhesion between the lubricant layer 18 and the carbon-based protective layer are further improved.

The film thickness of the protective layer 17 is preferably 1 nm to 7 nm. When the thickness of the protective layer 17 is 1 nm or more, the performance of the protective layer 17 is sufficiently obtained. The thickness of the protective layer 17 is preferably 7 nm or less from the viewpoint of reducing the thickness of the protective layer 17.

As a method for forming the protective layer 17, a sputtering method using a target material containing carbon, a chemical vapor deposition (CVD) method using a hydrocarbon raw material such as ethylene or toluene, an ion beam deposition (IBD) method, or the like can be used.

When a carbon-based protective layer is formed as the protective layer 17, it can be formed by, for example, a DC magnetron sputtering method. In particular, when a carbon-based protective layer is formed as the protective layer 17, it is preferable to form an amorphous carbon protective layer by a plasma CVD method. The amorphous carbon protective layer formed by the plasma CVD method has a uniform surface and small roughness.

"Lubricant Layer"

The lubricant layer 18 prevents contamination of the magnetic recording medium 10. Further, the lubricant layer 18 reduces the frictional force of the magnetic head of the magnetic recording/reproducing apparatus that slides on the magnetic recording medium 10, and improves the durability of the magnetic recording medium 10.

The lubricant layer 18 is formed on and is in contact with the protective layer 17, as shown in FIG. 1. The lubricant layer 18 includes the above-described fluorine-containing ether compound.

When the protective layer 17 disposed under the lubricant layer 18 is a carbon-based protective layer, in particular, the lubricant layer 18 is bonded to the protective layer 17 with a high bonding strength. As a result, even when the lubricant layer 18 is thin, it is easy to obtain the magnetic recording medium 10 in which the surface of the protective layer 17 is coated with a high coverage rate, and contamination of the surface of the magnetic recording medium 10 can be effectively prevented.

The average film thickness of the lubricant layer 18 is preferably from 0.5 nm (5 Å) to 3 nm (30 Å), more preferably from 0.5 nm (5 Å) to 2 nm (20 Å). When the average film thickness of the lubricant layer 18 is 0.5 nm or more, the lubricant layer 18 is formed with a uniform film thickness without forming an island shape or a mesh shape. For this reason, the surface of the protective layer 17 can be covered with the lubricant layer 18 at a high coverage rate. Moreover, by making the average film thickness of the lubricant layer 18 to be 3 nm or less, the lubricant layer 18 can be made sufficiently thin, and the floating height of the magnetic head can be sufficiently reduced.

When the surface of the protective layer 17 is not covered with a sufficiently high coverage by the lubricant layer 18, the environmental substance adsorbed on the surface of the magnetic recording medium 10 passes through the gap of the lubricant layer 18 and enters under the lubricant layer 18. Environmental substances that enter the lower layer of the lubricant layer 18 are adsorbed and bonded to the protective layer 17 to form contaminants. Then, during magnetic recording and reproducing, the contaminant (aggregation component) adheres (transfers) to the magnetic head as smear to damage the magnetic head or to reduce the magnetic recording and reproducing characteristics of the magnetic recording and reproducing apparatus.

Examples of the environmental substances which produce the contaminants include siloxane compounds (cyclic siloxane or linear siloxane), ionic impurities, hydrocarbons having a relatively high molecular weight such as octacosane, and plasticizers such as dioctyl phthalate. Examples of metal ions contained in the ionic impurities include sodium ions, potassium ions, and the like. Examples of inorganic ions contained in the ionic impurities include chlorine ions, bromine ions, nitrate ions, sulfate ions, ammonium ions, and the like. Examples of organic ions contained in the ionic impurities include oxalate ions, formate ions, and the like.

"Method of Forming Lubricant Layer"

As a method of forming the lubricant layer 18, for example, a method of preparing a magnetic recording medium in the middle of production in which the layers up to the protective layer 17 are formed on the substrate 11, applying a lubricant layer-forming solution on the protective layer 17, and then drying the layer, may be used.

The lubricant layer-forming solution can be obtained by dispersing and dissolving the lubricant for magnetic recording medium of the above-described embodiment in a solvent as necessary to obtain a viscosity and concentration suitable for the coating method. Examples of solvents used in the lubricant layer-forming solution include fluorinated solvents such as Vertrel (registered trademark) XF (trade name, manufactured by Mitsui DuPont Fluorochemical Co., Ltd.).

The method for applying the lubricant layer-forming solution is not particularly limited, and examples thereof include a spin-coating method, a spray method, a paper coating method, and a dip method.

When using the dip method, for example, the following method can be used. First, the substrate 11 on which the layers up to the protective layer 17 are formed is dipped in the lubricant layer-forming solution placed in the dipping tank of the dip coater. Subsequently, the substrate 11 is pulled up from the dipping tank at a predetermined speed. Thus, the lubricant layer-forming solution is applied to the surface of the protective layer 17 on the substrate 11.

By using the dip method, the lubricant layer-forming solution can be applied uniformly to the surface of the protective layer 17, and the lubricant layer 18 can be formed on the protective layer 17 with a uniform film thickness.

In the present embodiment, it is preferable to heat the substrate 11 on which the lubricant layer 18 is formed. By performing the heat treatment, the adhesion between the lubricant layer 18 and the protective layer 17 is improved, and the adhesive strength between the lubricant layer 18 and the protective layer 17 is improved.

The heat treatment temperature is preferably 100 to 180° C. When the heat treatment temperature is 100° C. or higher, the effect of improving the adhesion between the lubricant layer 18 and the protective layer 17 is sufficiently obtained. Moreover, thermal decomposition of the lubricant layer 18 can be prevented by setting the heat treatment temperature to 180° C. or lower. The heat treatment time is preferably 10 to 120 minutes.

In the present embodiment, in order to further improve the adhesion of the lubricant layer 18 to the protective layer 17, the lubricant layer 18 of the substrate 11 before or after the heat treatment may be subjected to a process of irradiating ultraviolet rays (UV).

The magnetic recording medium 10 of the present embodiment is obtained by sequentially providing at least a magnetic layer 16, a protective layer 17, and a lubricant layer 18 on a substrate 11. In the magnetic recording medium 10 of the present embodiment, the lubricant layer 18 containing the above-mentioned fluorine-containing ether compound is formed on and in contact with the protective layer 17. The lubricant layer 18, in which surface unevenness is suppressed, has excellent chemical substance resistance and wear resistance, and can be further thinned. Therefore, the magnetic recording medium 10 according to the present embodiment can contribute to a reduction in magnetic spacing. For this reason, the magnetic recording medium 10 of the present embodiment is particularly suitable as a magnetic disk mounted in a LUL type (load unload type) magnetic disk device.

EXAMPLE

Hereinafter, the present invention will be described more specifically with reference to examples and comparative examples. In addition, this invention is not limited only to the following examples.

Example 1

A compound represented by the formula (A) (In the formula (A), m indicating an average degree of polymerization is 4.5, and n indicating an average degree of polymerization is 4.5.) was obtained by the following method.

First, a compound represented by the formula (12) was synthesized by the following method. A compound represented by the formula (11) was synthesized by reacting 2-thiophenemethanol with epibromohydrin. The obtained compound (11) was hydrolyzed and the primary hydroxyl group of the obtained compound was protected with a t-butyldimethylsilyl group. The secondary hydroxyl group was then protected with a methoxymethyl group and the t-butyldimethylsilyl group was removed from the obtained compound. Finally, the resulting primary hydroxyl group was reacted with epibromohydrin to synthesize Compound (12).

[Chemical Formula 17]

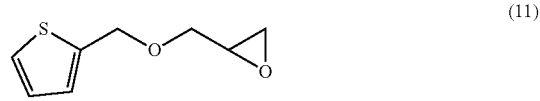

(11)

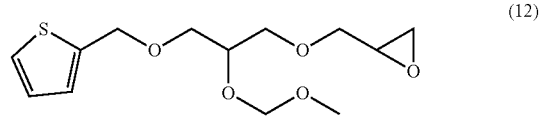

(12)

A compound represented by formula (13) was synthesized by reacting ethylene glycol tert-butyl ether with epibromohydrin.

[Chemical Formula 18]

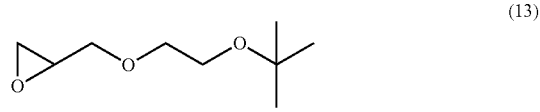

(13)

In a 200 mL eggplant flask under a nitrogen gas atmosphere, a fluoropolyether represented by HOCH$_2$CF$_2$O (CF$_2$CF$_2$O)$_h$(CF$_2$O)$_i$CF$_2$CH$_2$OH (In the formula, h indicating an average degree of polymerization is 4.5, and i indicating an average degree of polymerization is 4.5.) (number average molecular weight: 1000; molecular weight distribution: 1.1) (40.0 g), a compound represented by the formula (12) (6.92 g), and t-BuOH (tert-butyl alcohol) (40.0 mL) were charged and stirred at room temperature until the mixture became uniform. Then, t-BuOK (potassium tertiary butoxide) (1.35 g) was added to the eggplant flask, and the mixture was heated to 70° C. and stirred for 8 hours to react.

Thereafter, the obtained reaction product was cooled to 25° C., water was added thereto, and then Vertrel (registered trademark) XF (hereinafter referred to as "Vertrel XF") manufactured by Mitsui DuPont Fluorochemical Co., Ltd. was added to extract the organic layer, and washed with water. The organic layer was dried by adding anhydrous sodium sulfate, the desiccant was filtered off, and the filtrate was concentrated. The residue was purified by silica gel column chromatography to obtain a compound represented by the following formula (14) (17.4 g).

[Chemical Formula 19]

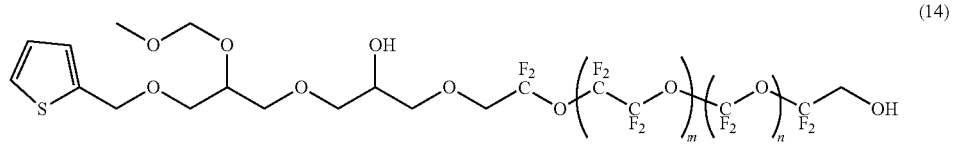

(14)

(In the formula (14), m indicating an average degree of polymerization is 4.5, and n indicating an average degree of polymerization is 4.5.)

In a 200 mL eggplant flask under a nitrogen gas atmosphere, a compound represented by the formula (14) (17.4 g), a compound represented by the formula (13) (2.67 g), and t-BuOH (tert-butyl alcohol) (65.0 mL) were charged and stirred at room temperature until the mixture became uniform. Then, t-BuOK (potassium tertiary butoxide) (0.235 g) was added to the eggplant flask, and the mixture was heated to 70° C. and stirred for 16 hours to react.

Thereafter, the obtained reaction product was cooled to 25° C., water was added thereto, then Vertrel XF was added thereto to extract the organic layer, and washed with water. The organic layer was dried by adding anhydrous sodium sulfate, the desiccant was filtered off, and the filtrate was concentrated.

To the resulting residue, water (3.3 mL) and trifluoroacetic acid (21.5 mL) were added at room temperature and the mixture was stirred at room temperature for 6 hours. Water and trifluoroacetic acid were distilled off at a temperature of 35° C. or lower, 5% sodium bicarbonate water (100 mL) was added to the obtained residue, the organic layer was extracted with Vertrel XF, and the organic layer was washed with water and concentrated.

To the resulting residue, methanol (56 mL) and 1 mol/L aqueous sodium hydroxide solution (56 mL) were added and the mixture was stirred at room temperature for 1 hour.

After distilling off methanol, Vertrel XF was added to extract the organic layer and the organic layer was washed with water. The organic layer was dried by adding anhydrous sodium sulfate, the desiccant was filtered off, and the filtrate was concentrated. The residue was purified by silica gel column chromatography to give 11.0 g of Compound (A).

Obtained Compound (A) was subjected to $^1$H-NMR and $^{19}$F-NMR measurements, and its structure was identified based on the following results.

$^1$H-NMR (acetone-$d_6$): δ [ppm]=3.44-3.78 (17H), 3.85-4.20 (12H), 6.90 (2H), 7.23 (1H)

$^{19}$F-NMR (acetone-$d_6$): δ [ppm]=−51.99 to −55.72 (9F), −78.48 (2F), −80.66 (2F), −89.16 to −91.14 (18F)

Example 2

A compound represented by the formula (B) (In the formula (B), m indicating an average degree of polymerization is 4.5, and n indicating an average degree of polymerization is 4.5.) was obtained by the following method.

First, a compound represented by the formula (16) was synthesized by the following method. A compound represented by the formula (15) was synthesized by reacting 2-thiophene ethanol with epibromohydrin. The obtained compound (15) was hydrolyzed and the primary hydroxyl group of the resulting compound was protected with a t-butyldimethylsilyl group. The secondary hydroxyl group was then protected with a methoxymethyl group and the t-butyldimethylsilyl group was removed from the resulting compound. Finally, the resulting primary hydroxyl group was reacted with epibromohydrin to synthesize Compound (16).

[Chemical Formula 20]

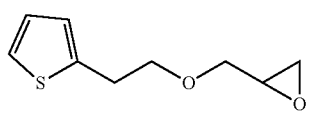

(15)

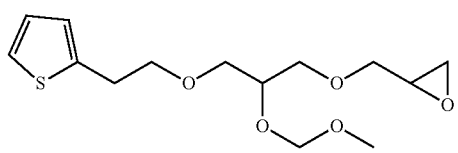

(16)

Then, the same procedure as in Example 1 was performed except that instead of the compound represented by the formula (12) used in Example 1, 7.26 g of the compound represented by the formula (16) was used to obtain 11.2 g of Compound (B).

Obtained Compound (B) was subjected to $^1$H-NMR measurement, and its structure was identified by the following results.

$^1$H-NMR (acetone-$d_6$): δ [ppm]=3.07 (2H), 3.44-3.78 (19H), 3.85-4.20 (10H), 6.90 (2H), 7.23 (1H)

Example 3

A compound represented by the formula (C) (In the formula (C), m indicating an average degree of polymerization is 4.5, and n indicating an average degree of polymerization is 4.5.) was obtained by the following method.

First, a compound represented by the formula (18) was synthesized by the following method. A compound represented by the formula (17) was synthesized by reacting 2-thiophene propanol with epibromohydrin. The obtained compound (17) was hydrolyzed and the primary hydroxyl group of the obtained compound was protected with a t-butyldimethylsilyl group. The secondary hydroxyl group was then protected with a methoxymethyl group and the t-butyldimethylsilyl group was removed from the obtained compound. Finally, the resulting primary hydroxyl group was reacted with epibromohydrin to synthesize Compound (18).

[Chemical Formula 21]

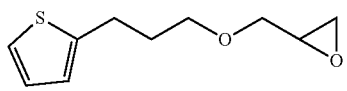

(17)

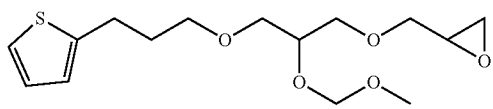

(18)

Then, the same procedure as in Example 1 was performed except that instead of the compound represented by the formula (12) used in Example 1, 7.59 g of the compound represented by the formula (18) was used to obtain 11.9 g of Compound (C).

Obtained Compound (C) was subjected to $^1$H-NMR measurement, and its structure was identified by the following results.

$^1$H-NMR (acetone-$d_6$): δ [ppm]=1.95 (2H), 2.91 (2H), 3.44-3.78 (19H), 3.85-4.20 (10H), 6.90 (2H), 7.23 (1H)

Example 4

A compound represented by the formula (D) (In the formula (D), m indicating an average degree of polymerization is 4.5, and n indicating an average degree of polymerization is 4.5.) was obtained by the following method.

First, a compound represented by the formula (20) was synthesized by the following method. A compound represented by the formula (19) was synthesized by reacting 3-thiophenemethanol with epibromohydrin. The obtained compound (19) was hydrolyzed and the primary hydroxyl group of the obtained compound was protected with a t-butyldimethylsilyl group. The secondary hydroxyl group was then protected with a methoxymethyl group and the t-butyldimethylsilyl group was removed from the obtained compound. Finally, the resulting primary hydroxyl group was reacted with epibromohydrin to synthesize Compound (20).

[Chemical Formula 22]

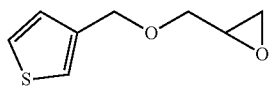

(19)

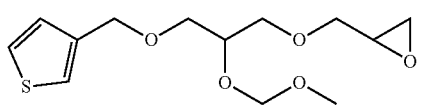

(20)

Then, the same procedure as in Example 1 was performed except that instead of the compound represented by the formula (12) used in Example 1, 6.92 g of the compound represented by the formula (20) was used to obtain 11.3 g of Compound (D).

Obtained Compound (D) was subjected to $^1$H-NMR measurement, and its structure was identified by the following results.

$^1$H-NMR (acetone-$d_6$): δ [ppm]=3.44-3.78 (17H), 3.85-4.20 (12H), 7.05 (2H), 7.43 (1H)

Example 5

A compound represented by the formula (E) (In the formula (E), m indicating an average degree of polymerization is 4.5, and n indicating an average degree of polymerization is 4.5.) was obtained by the following method.

First, a compound represented by the formula (22) was synthesized by the following method. A compound represented by the formula (21) was synthesized by reacting 3-thiophene ethanol with epibromohydrin. The obtained compound (21) was hydrolyzed and the primary hydroxyl group of the obtained compound was protected with a t-butyldimethylsilyl group. The secondary hydroxyl group was then protected with a methoxymethyl group and the t-butyldimethylsilyl group was removed from the obtained compound. Finally, the resulting primary hydroxyl group was reacted with epibromohydrin to synthesize Compound (22).

[Chemical Formula 23]

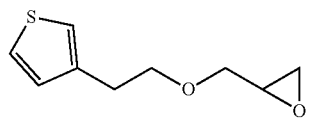

(21)

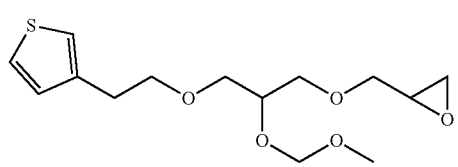

(22)

Then, the same procedure as in Example 1 was performed except that instead of the compound represented by the formula (12) used in Example 1, 7.26 g of the compound represented by the formula (22) was used to obtain 11.5 g of Compound (E).

Obtained Compound (E) was subjected to $^1$H-NMR measurement, and its structure was identified by the following results.

$^1$H-NMR (acetone-$d_6$): δ [ppm]=2.94 (2H), 3.44-3.78 (19H), 3.85-4.20 (10H), 7.05 (2H), 7.43 (1H)

Example 6

A compound represented by the formula (F) (In the formula (F), m indicating an average degree of polymerization is 4.5, and n indicating an average degree of polymerization is 4.5.) was obtained by the following method.

First, a reaction product of ethylene glycol tert-butyl ether and allyl glycidyl ether was oxidized to synthesize a compound represented by the following formula (23).

Then, the same procedure as in Example 2 was performed except that instead of the compound represented by the formula (13) used in Example 2, 3.81 g of the compound represented by the formula (23) was used to obtain 12.5 g of Compound (F).

[Chemical Formula 24]

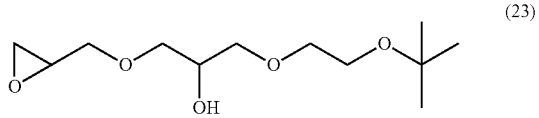
(23)

Obtained Compound (F) was subjected to $^1$H-NMR measurement, and its structure was identified by the following results.

$^1$H-NMR (acetone-$d_6$): δ [ppm]=3.07 (2H), 3.44-3.78 (23H), 3.85-4.20 (12H), 6.90 (2H), 7.23 (1H)

Example 7

A compound represented by the formula (G) (In the formula (G), m indicating an average degree of polymerization is 4.5, and n indicating an average degree of polymerization is 4.5.) was obtained by the following method.

First, a compound represented by the formula (24) was synthesized by the following method. A compound represented by the formula (16) was hydrolyzed, and the primary hydroxyl group of the obtained compound was protected with a t-butyldimethylsilyl group. Then, the two secondary hydroxyl groups were protected with a methoxymethyl group, respectively, and the t-butyldimethylsilyl group was removed from the resulting compound.

Finally, the resulting primary hydroxyl group was reacted with epibromohydrin to synthesize a compound represented by the following formula (24).

[Chemical Formula 25]

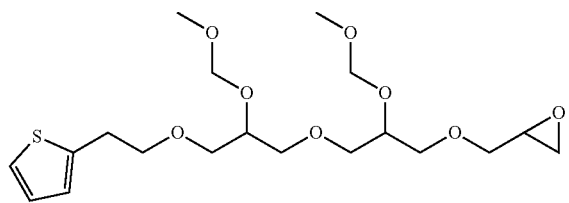
(24)

Then, the same procedure as in Example 1 was performed except that instead of the compound represented by the formula (12) used in Example 1, 10.1 g of the compound represented by the formula (24) was used, and instead of the compound represented by the formula (13) used in Example 1, 3.81 g of the compound represented by the formula (23) was used, thereby obtaining 12.9 g of Compound (G).

Obtained Compound (G) was subjected to $^1$H-NMR measurement, and its structure was identified by the following results.

$^1$H-NMR (acetone-$d_6$): δ [ppm]=3.07 (2H), 3.44-3.78 (27H), 3.85-4.20 (14H), 6.90 (2H), 7.23 (1H)

Example 8

A compound represented by the formula (H) (In the formula (H), m indicating an average degree of polymerization is 4.5, and n indicating an average degree of polymerization is 4.5.) was obtained by the following method.

First, a compound represented by the following formula (25) was synthesized by reacting propanediol tert-butyl ether with epibromohydrin.

[Chemical Formula 26]

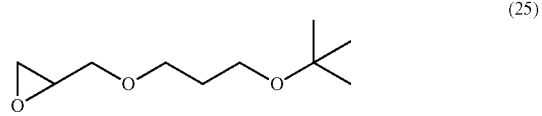
(25)

Then, the same procedure as in Example 2 was carried out except that instead of the compound represented by the formula (13) used in Example 2, 2.89 g of the compound represented by the formula (25) was used to obtain 11.8 g of Compound (H).

Obtained Compound (H) was subjected to $^1$H-NMR measurement, and its structure was identified by the following results.

$^1$H-NMR (acetone-$d_6$): δ [ppm]=1.83 (2H), 3.07 (2H), 3.44-3.78 (19H), 3.85-4.20 (10H), 6.90 (2H), 7.23 (1H)

Example 9

A compound represented by the formula (I) (In the formula (I), m indicating an average degree of polymerization is 4.5, and n indicating an average degree of polymerization is 4.5.) was obtained by the following method. 2,2,3,3-tetrafluoro-1, 4-butanediol was reacted with 3,4-dihydro-2H-pyran to protect one hydroxyl group with a tetrahydropyranyl group, and then epibromohydrin was reacted to synthesize a compound represented by the following formula (26).

Then, the same procedure as in Example 2 was performed except that instead of the compound represented by the formula (13) used in Example 2, 4.64 g of the compound represented by the formula (26) was used to obtain 12.9 g of Compound (I).

[Chemical Formula 27]

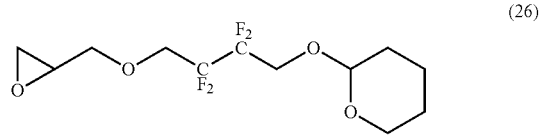
(26)

Obtained Compound (I) was subjected to $^1$H-NMR measurement, and its structure was identified by the following results.

$^1$H-NMR (acetone-$d_6$): δ [ppm]=3.07 (2H), 3.44-3.78 (15H), 3.85-4.20 (14H), 6.90 (2H), 7.23 (1H)

Example 10

A compound represented by the formula (J) (In the formula (J), m indicating an average degree of polymerization is 4.5, and n indicating an average degree of polymerization is 4.5.) was obtained by the following method.

3-butene-1-ol was reacted with 3,4-dihydro-2H-pyran to protect a hydroxyl group with a tetrahydropyranyl group, and then oxidized with methachloroperbenzoic acid to synthesize a compound represented by the following formula (27).

[Chemical Formula 28]

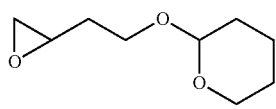
(27)

Then, the same procedure as in Example 2 was performed except that instead of the compound represented by the formula (13) used in Example 2, 2.64 g of the compound represented by the formula (27) was used to obtain 11.2 g of Compound (J).

Obtained Compound (J) was subjected to $^1$H-NMR measurement, and its structure was identified by the following results.

$^1$H-NMR (acetone-$d_6$): δ [ppm]=1.68 (2H), 3.07 (2H), 3.44-3.78 (16H), 3.85-4.20 (9H), 6.90 (2H), 7.23 (1H)

Example 11

A compound represented by the formula (K) (In the formula (K), v indicating an average degree of polymerization is 4.5.) was obtained by the following method.

The same procedure as in Example 2 was carried out except that instead of the fluoropolyether represented by $HOCH_2CF_2O(CF_2CF_2O)_h(CF_2O)_iCF_2CH_2OH$ (In the formula, h indicating an average degree of polymerization is 4.5, and i indicating an average degree of polymerization is 4.5.) (number average molecular weight: 1000; molecular weight distribution: 1.1) used in Example 2, 40.0 g of a fluoropolyether represented by $HOCH_2CF_2CF_2O(CF_2CF_2CF_2O)_jCF_2CF_2CH_2OH$ (In the formula, j indicating an average degree of polymerization is 4.5.) was used, to obtain 10.1 g of Compound (K).

Obtained Compound (K) was subjected to $^1$H-NMR and $^{19}$F-NMR measurements, and its structure was identified based on the following results.

$^1$H-NMR (acetone-$d_6$): δ [ppm]=3.08 (2H), 3.44-3.80 (19H), 3.85-4.20 (10H), 6.93 (2H), 7.26 (1H)

$^{19}$F-NMR (acetone-$d_6$): δ [ppm]=−83.70 (18F), −86.55 (4F), −124.21 (4F), −129.73 (9F)

Example 12

A compound represented by the formula (L) (In the formula (L), m indicating an average degree of polymerization is 7.) was obtained by the following method.

The same procedure as in Example 2 was carried out except that instead of the fluoropolyether represented by $HOCH_2CF_2O(CF_2CF_2O)_h(CF_2O)_iCF_2CH_2OH$ (In the formula, h indicating an average degree of polymerization is 4.5, and i indicating an average degree of polymerization is 4.5.) (number average molecular weight: 1000; molecular weight distribution: 1.1) used in Example 2, 40.0 g of a fluoropolyether represented by $HOCH_2CF_2O(CF_2CF_2O)_kCF_2CH_2OH$ (In the formula, k representing an average degree of polymerization is 7.) was used, to obtain 10.1 g of Compound (L).

Obtained Compound (L) was subjected to $^1$H-NMR and $^{19}$F-NMR measurements, and its structure was identified based on the following results.

$^1$H-NMR (acetone-$d_6$): δ [ppm]=3.04 (2H), 3.40-3.79 (19H), 3.85-4.25 (10H), 6.92 (2H), 7.21 (1H)

$^{19}$F-NMR (acetone-$d_6$): δ [ppm]=−78.57(4F), −89.24 to −89.57(28F)

Comparative Example 1

A compound represented by the following formula (AA) was synthesized by the method described in Patent Document 4.

[Chemical Formula 29]

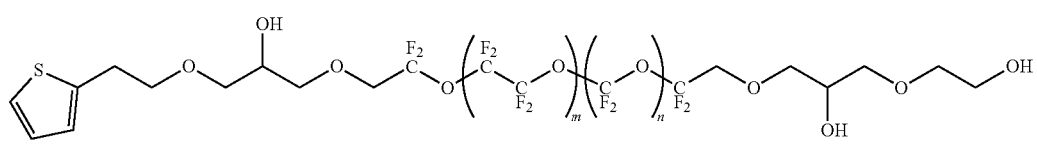
(AA)

(In the formula (AA), m indicating an average degree of polymerization is 4.5, and n indicating an average degree of polymerization is 4.5.)

Comparative Example 2

A compound represented by the following formula (AB) was synthesized by the method described in Patent Document 4.

[Chemical Formula 30]

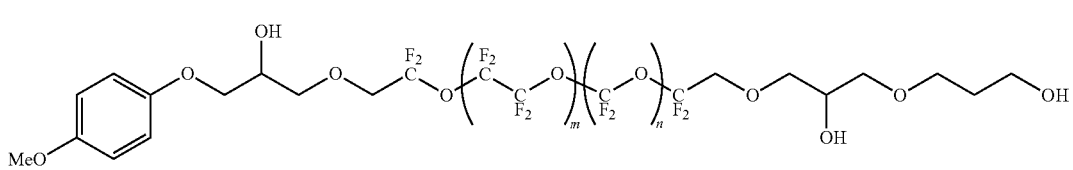
(AB)

(In the formula (AB), m indicating an average degree of polymerization is 4.5, and n indicating an average degree of polymerization is 4.5. Me is a methyl group.)

Comparative Example 3

A compound represented by the following formula (AC) was synthesized by the method described in Patent Document 4.

[Chemical Formula 31]

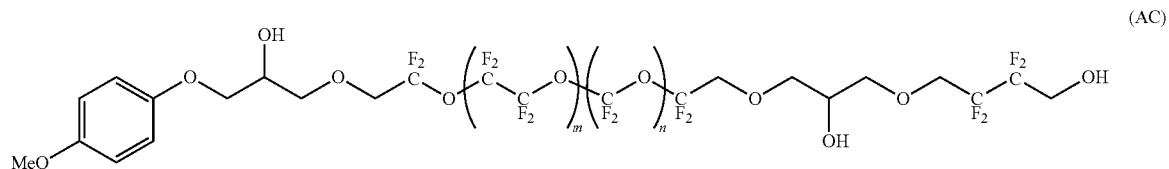

(AC)

(In the formula (AC), m indicating an average degree of polymerization is 4.5, and n indicating an average degree of polymerization is 4.5. Me is a methyl group.)

Comparative Example 4

A compound represented by the following formula (AD) was synthesized by the method described in Patent Document 4.

[Chemical Formula 32]

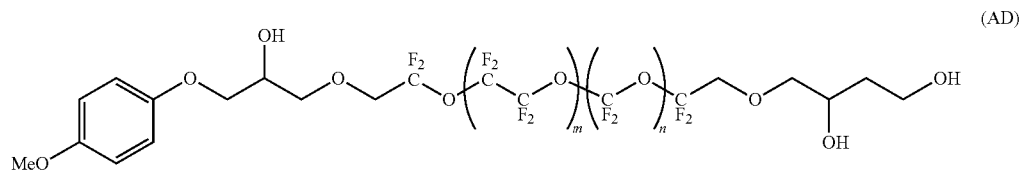

(AD)

(In the formula (AD), m indicating an average degree of polymerization is 4.5, and n indicating an average degree of polymerization is 4.5. Me is a methyl group.)

Comparative Example 5

A compound represented by the following formula (AE) was synthesized by the method described in Patent Document 4.

[Chemical Formula 33]

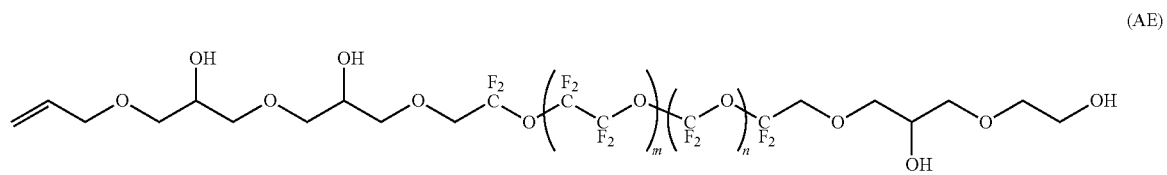

(AE)

(In the formula (AE), m indicating an average degree of polymerization is 4.5, and n indicating an average degree of polymerization is 4.5.)

Number average molecular weights of the compounds of Examples 1 to 12 and Comparative Examples 1 to 5 thus obtained were determined by the $^1$H-NMR and $^{19}$F-NMR measurements described above. The results are shown in Table 1. It is estimated that the value of number average molecular weight of the synthesized compounds varies by about 1 to 5 depending on the molecular weight distribution of the fluoropolyether used as the raw material of the compound and the difference in the operation in synthesizing the compound.

TABLE 1

| Compound | | Number average molecular weight | Film thickness (Å) | Time Until Coefficient of Friction Sharply Increases (sec) | Si Adsorption amount | TDp (mW) |
|---|---|---|---|---|---|---|
| Example 1 | (A) | 1364 | 8.5 | 643 | 0.63 | 51.6 |
| Example 2 | (B) | 1379 | 8.5 | 671 | 0.63 | 51.6 |
| Example 3 | (C) | 1391 | 8.5 | 689 | 0.66 | 51.6 |
| Example 4 | (D) | 1366 | 8.5 | 656 | 0.65 | 51.6 |
| Example 5 | (E) | 1377 | 8.5 | 682 | 0.65 | 51.6 |
| Example 6 | (F) | 1449 | 8.5 | 738 | 0.58 | 51.7 |
| Example 7 | (G) | 1529 | 8.5 | 743 | 0.51 | 51.7 |
| Example 8 | (H) | 1391 | 8.5 | 672 | 0.63 | 51.6 |
| Example 9 | (I) | 1479 | 8.5 | 711 | 0.58 | 51.6 |
| Example 10 | (J) | 1342 | 8.5 | 609 | 0.67 | 51.7 |
| Example 11 | (K) | 1375 | 8.5 | 652 | 0.66 | 51.6 |
| Example 12 | (L) | 1378 | 8.5 | 667 | 0.64 | 51.6 |
| Comparative Example 1 | (AA) | 1302 | 8.5 | 425 | 1.01 | 50.8 |
| Comparative Example 2 | (AB) | 1310 | 8.5 | 478 | 1.07 | 50.8 |
| Comparative Example 3 | (AC) | 1400 | 8.5 | 481 | 1.01 | 50.8 |
| Comparative Example 4 | (AD) | 1268 | 8.5 | 412 | 1.12 | 50.8 |
| Comparative Example 5 | (AE) | 1304 | 8.5 | 431 | 1.00 | 50.9 |

Next, a lubricant layer-forming solution was prepared by using the compounds obtained in Examples 1 to 12 and Comparative Examples 1 to 5 by the method described below. Then, using the obtained lubricant layer-forming solution, a lubricant layer of a magnetic recording medium was formed by the following method, and magnetic recording media of Examples 1 to 12 and Comparative Examples 1 to 5 were obtained.

"Lubricant Layer-Forming Solution"

The compounds obtained in Examples 1 to 12 and Comparative Examples 1 to 5 were each dissolved in Vertrel (registered trademark) XF (trade name, manufactured by Mitsui DuPont Fluoro Chemical Co., Ltd.), which is a fluorine-based solvent, and diluted with Vertrel XF so that the film thickness would be 8.5 Å to 10 Å when applied onto the protective layer, and a lubricant layer-forming solution in which the concentration of the compounds was 0.001% by mass to 0.01% by mass was obtained.

"Magnetic Recording Media"

A magnetic recording medium in which an adhesion layer, a soft magnetic layer, a first base layer, a second base layer, a magnetic layer, and a protective layer were sequentially provided on a substrate having a diameter of 65 mm was prepared. The protective layer was made of carbon.

The lubricant layer-forming solutions of Examples 1 to 12 and Comparative Examples 1 to 5 were applied by a dip method on the protective layer of the magnetic recording medium on which the layers up to the protective layer were formed.

Thereafter, the magnetic recording medium coated with the lubricant layer-forming solution was placed in a thermostatic chamber at 120° C. and subjected to heat treatment for 10 minutes. As a result, a lubricant layer was formed on the protective layer to obtain a magnetic recording medium.

(Film Thickness Measurement)

Film thicknesses of the lubricant layers of the obtained magnetic recording media of Examples 1 to 12 and Comparative Examples 1 to 5 were measured by the following methods.

FT-IR (trade name: Nicolet iS50, manufactured by Thermo Fisher Scientific) was used to measure the peak height of the C—F stretching vibrations of the lubricant layer. Next, a film thickness of the lubricant layer was calculated from the measured value of the peak height in the C—F stretching vibrations of the lubricant layer by using the correlation equation calculated by the following method. The results are shown in Table 1.

(Calculation Method of Correlation Equation)

On a substrate having a diameter of 65 mm, a lubricant layer having a thickness of 6 to 20 Å (2 Å increment) was formed on the surface of a disk in which an adhesion layer, a soft magnetic layer, a first base layer, a second base layer, a magnetic layer and a protective layer were sequentially provided.

Thereafter, for each disk on which the lubricant layer was formed, the increase of film thickness from the surface of the disk on which the lubricant layer was not formed was measured using an ellipsometer to determine the film thickness of the lubricant layer. The peak height of C—F stretching vibrations was measured using FT-IR (trade name: Nicolet iS50, manufactured by Thermo Fisher Scientific) for each disk on which the lubricant layer was formed.

Then, the correlation between the peak height obtained by FT-IR and the film thickness of the lubricant layer obtained by using an ellipsometer was obtained.

The main chain of the fluorine-containing ether compound contained in the lubricant layer is mainly formed of C and F. However, the density of C—F in a molecule varies with the type of fluorine-containing ether compound. Therefore, even if fluorine-containing ether compounds have the same peak height in C—F stretching vibrations obtained by using FT-IR, the film thicknesses of the lubricant layers formed by using the fluorine-containing ether compounds may be different.

Also, wear resistance tests, chemical substance resistance tests and touchdown power measurements were performed on the magnetic recording media of Examples 1 to 12 and Comparative Examples 1 to 5 by the methods described below. The results are shown in Table 1.

(Wear Resistance Test)

Using a pin-on-disk type friction and wear tester, an alumina ball having a diameter of 2 mm was used as a contact and was slid on the lubricant layer of the magnetic recording medium with a load of 40 gf at a sliding speed of 0.25 m/sec, to measure a coefficient of friction of the surface of the lubricant layer. The sliding time until the coefficient of friction sharply increases was measured on the surface of the lubricant layer. The sliding time until the coefficient of friction sharply increases was measured four times for the lubricant layer of each magnetic recording medium, and an average value (time) thereof was used as an indicator of the wear resistance of the lubricant coating film.

The time until the coefficient of friction sharply increases can be used as an indicator of the wear resistance of the lubricant layer for the following reason. In the lubricant layer of the magnetic recording medium, wear progresses according to use of the magnetic recording medium. When the lubricant layer disappears due to wear, the contact and the protective layer are in direct contact with each other to cause the coefficient of friction to sharply increase.

(Chemical Substance Resistance Test)

The following evaluation method was used to examine the contamination of magnetic recording media with environmental substances that generate contaminants in a high temperature environment. In the following evaluation method, Si ions were used as the environmental substance, and the amount of Si adsorption was measured as the amount of contaminants that contaminate the magnetic recording medium and that were generated by the environmental substance.

Specifically, the magnetic recording medium to be evaluated was held for 240 hours in the presence of a siloxane-based Si rubber in a high-temperature environment at a temperature of 85° C. and a humidity of 0%. Next, the amount of Si adsorption existing on the surface of the magnetic recording medium was analyzed and measured using secondary ion mass spectrometry (SIMS), and the degree of contamination by Si ions was evaluated based on the amount of Si adsorption. The Si adsorption amount was evaluated using numerical values when the result of Comparative Example 5 was set to 1.00. The results are shown in Table 1.

(Touchdown Power Measurement)

As an evaluation index of magnetic spacing, which is the distance between a magnetic head and a recording layer of a magnetic disk, a touchdown power (TDp) was measured. The measurement of TDp was performed using a write tester (DFH Tester) as follows.

The magnetic recording medium to be evaluated was rotated at 5400 rpm, and a write element (DFH element) was arranged at a position with a radius of 18 mm from the center so as to face each other. Thereafter, the heater power of the DFH element was gradually increased, and the DFH element was thermally expanded by heat generation of the heater. The heater power at the time when the tip of the DFH element, protruded by the thermal expansion of the DFH element, came into contact with the lubricant layer of the magnetic recording medium was measured as TDp (mW in units).

The contact between the tip of the DFH element and the lubricant layer of the magnetic recording medium was detected by an acoustic emission (AE) sensor.

Generally, when the thickness of the lubricant layer is reduced, the TDp required for the write element (DFH element) to contact the surface of the magnetic recording medium (lubricant layer) is increased. On the other hand, TDp becomes small when unevenness exists on the surface of the magnetic recording medium (lubricant layer).

The film thickness of the lubricant layer shown in Table 1 is a value calculated using FT-IR and is an average film thickness. Therefore, even if the film thickness of the lubricant layer shown in Table 1 is the same, if the maximum thickness of the lubricant layer is different depending on the presence or absence of unevenness on the surface of the lubricant layer, the TDp is a different value.

As shown in Table 1, the magnetic recording media of Examples 1 to 12 had a longer sliding time until the coefficient of friction rapidly increased than the magnetic recording media of Comparative Examples 1 to 5, and had a better wear resistance.

Also, as shown in Table 1, it was found that the magnetic recording media of Examples 1 to 12 had a smaller Si adsorption amount than the magnetic recording media of Comparative Examples 1 to 5, and were less likely to be contaminated by environmental substances in a high-temperature environment even if the film thicknesses were thin.

Also, as shown in Table 1, it was found that the magnetic recording media of Examples 1 to 12 had a larger touchdown power (TDp) than the magnetic recording media of Comparative Examples 1 to 5, and the magnetic spacing can be reduced.

More specifically, in Comparative Example 1, since a compound in which the number of hydroxyl groups provided between the perfluoropolyether chain and the thiophene alkyl group is 1 was used, wear resistance and chemical substance resistance were insufficient, and touchdown power was reduced.

In Comparative Examples 2 to 4, since compounds in which a thiophene alkyl group is not arranged and the number of hydroxyl groups present at one end of the perfluoropolyether chain is 1 were used, wear resistance and chemical substance resistance were insufficient, and touchdown powers were reduced.

In Comparative Example 5, since a compound in which a thiophene alkyl group is not arranged was used, wear resistance and chemical substance resistance were insufficient, and touchdown power was reduced.

It is presumed that the effect shown in Table 1 is obtained in the magnetic recording media of Examples 1 to 12, because the lubricant layers contain the compounds represented by the formula (1), and the lubricant layers have good adhesion to the protective layer and have a high coverage with suppressed surface unevenness.

INDUSTRIAL APPLICABILITY

A fluorine-containing ether compound capable of forming a lubricant layer having excellent wear resistance and chemical substance resistance even when the film is thinned and magnetic spacing is reduced, and can suitably be used as a material of a lubricant for magnetic recording media, is provided.

DESCRIPTION/EXPLANATION OF REFERENCES

10 . . . Magnetic recording medium,
11 . . . Substrate,
12 . . . Adhesion layer,
13 . . . Soft magnetic layer,
14 . . . First base layer,
15 . . . Second base layer,
16 . . . Magnetic layer,
17 . . . Protective layer,
18 . . . Lubricant layer.

The invention claimed is:

1. A fluorine-containing ether compound represented by the following formula (1),

wherein in the formula (1), $R^1$ is represented by the following formula (2);

$R^2$ is represented by the following formula (3);

$R^3$ is a perfluoropolyether chain; and $R^4$ is an organic end group different from $R^1$—$R^2$— and comprises two or three polar groups, wherein each polar group is bonded to a different carbon atom, and the carbon atoms to which the polar groups are bonded are bonded to one another via a linking group containing a carbon atom to which the polar group is not bonded,

[Chemical Formula 1]

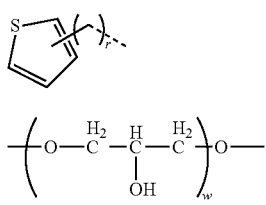

(2)

(3)

wherein in the formula (2), r represents an integer of 1 to 3; and in the formula (3), w represents 2 or 3.

2. The fluorine-containing ether compound according to claim 1, wherein all the polar groups of $R^4$ in the formula (1) are hydroxyl groups.

3. The fluorine-containing ether compound according to claim 1, wherein $R^4$ in the formula (1) is an end group represented by any one of the following formulae (4-1) to (4-4),

[Chemical Formula 2]

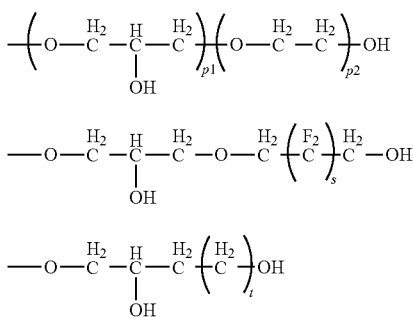

(4-1)

(4-2)

(4-3)

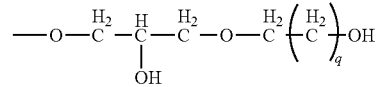

(4-4)

wherein in the formula (4-1), p1 represents an integer of 1 to 2, and p2 represents an integer of 1 to 5;

in the formula (4-2), s represents an integer of 2 to 5;

in the formula (4-3), t represents an integer of 1 to 5; and in the formula (4-4), q represents an integer of 2 to 5.

4. The fluorine-containing ether compound according to claim 1, wherein $R^3$ in the formula (1) is represented by the following formula (5)

[Chemical Formula 3]

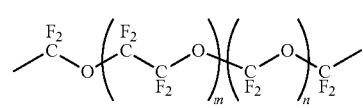

(5)

wherein in the formula (5), m and n indicate an average degree of polymerization, m represents 1 to 30, and n represents 0 to 30.

5. The fluorine-containing ether compound according to claim 1, wherein $R^3$ in the formula (1) is represented by the following formula (6) or the following formula (7),

[Chemical Formula 4]

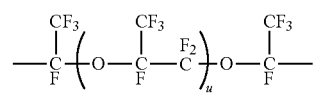

(6)

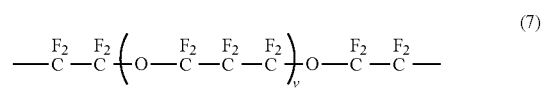

(7)

wherein in the formula (6), u indicates an average degree of polymerization and represents 1 to 30; and in the formula (7), v indicates an average degree of polymerization and represents 1 to 30.

6. The fluorine-containing ether compound according to claim 1, wherein the structure of the fluorine-containing ether compound is represented by the following formula (8),

[Chemical Formula 5]

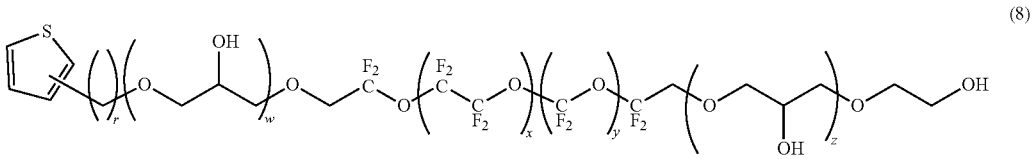

(8)

wherein in the formula (8), x and y indicate an average degree of polymerization, and each represents 1 to 20;

z represents 1 or 2;

w represents 2 or 3; and r represents an integer of 1 to 3.

7. The fluorine-containing ether compound according to claim 1, wherein r is 2.

8. The fluorine-containing ether compound according to claim 1, wherein a number average molecular weight is in the range of 500 to 10000.

9. A lubricant for magnetic recording media, comprising the fluorine-containing ether compound according to claim 1.

10. A magnetic recording medium in which at least a magnetic layer, a protective layer, and a lubricant layer are sequentially provided on a substrate, wherein the lubricant layer contains the fluorine-containing ether compound according to claim 1.

11. The magnetic recording medium according to claim 10, wherein an average film thickness of the lubricant layer is 0.5 nm to 2 nm.

* * * * *